United States Patent [19]

Tamura et al.

[11] Patent Number: 4,636,567
[45] Date of Patent: Jan. 13, 1987

[54] 4-SUBSTITUTED-2-AZETIDINONE COMPOUND

[75] Inventors: Toshinari Tamura, Tokyo; Hidenori Iwamoto; Makoto Yoshida, both of Saitama; Minoru Yamamoto, Kanagawa, all of Japan

[73] Assignee: Yamanouchi Pharmaceutical Co., Ltd., Tokyo, Japan

[21] Appl. No.: 785,169

[22] Filed: Oct. 7, 1985

Related U.S. Application Data

[62] Division of Ser. No. 592,866, Mar. 23, 1984.

[30] Foreign Application Priority Data

Mar. 25, 1983 [JP] Japan .................................. 58-48989
Nov. 25, 1983 [JP] Japan .................................. 58-221469
Nov. 25, 1983 [JP] Japan .................................. 58-221470

[51] Int. Cl.$^4$ .......................................... C07D 403/12
[52] U.S. Cl. ................................................. 548/336
[58] Field of Search ........................................ 548/336

[56] References Cited

U.S. PATENT DOCUMENTS 4,271,164 6/1981 Blankley et al. ..................... 548/336

Primary Examiner—Henry R. Jiles
Assistant Examiner—J. Richter
Attorney, Agent, or Firm—Burgess, Ryan & Wayne

[57] ABSTRACT

A novel-4-substituted-2-azetidinone compound shown by the general formula

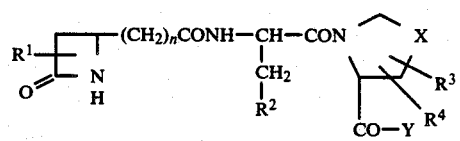

and salts thereof. The compounds of this invention have a strong CNS activity and are useful for improving a disturbance of consciousness in schizophrenia, a head injury, etc., or improving hypobulia, memory loss, etc.

1 Claim, No Drawings

4-SUBSTITUTED-2-AZETIDINONE COMPOUND

This is a division of application Ser. No. 592,866, filed Mar. 23, 1984. Priority is claimed under 35 USC 119 based on Japanese Applications Nos. 48,989/83 filed Mar. 25, 1983, 221469/83 filed Nov. 25, 1983 and 221470/83 filed Nov. 25, 1983, certified copies of which are presently being filed in the parent application U.S. Ser. No. 592,866.

DETAILED EXPLANATION OF THE INVENTION

This invention relates to 4-substituted-2-azetidinone compounds shown by following general formula

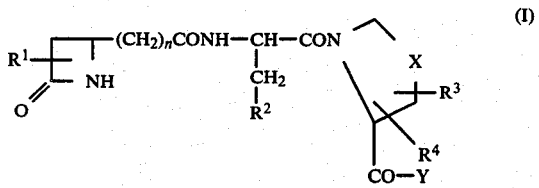

wherein $R^1$, $R^3$, and $R^4$, which may be the same or different, each represents a hydrogen atom or a lower alkyl group; $R^2$ represents an imidazole group shown by

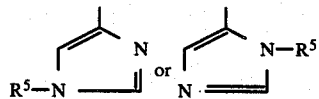

(wherein $R^5$ represents a hydrogen atom, a lower alkyl group, an aromatic acyl group, or an aryl group); n represents 0, 1, 2, or 3; X represents a methylene group, an ethylene group, an oxygen atom, or a sulfur atom; and Y represents a hydroxy group, a lower alkoxy group, an aralkoxy group, or an unsubstituted or substituted amino group shown by the formula

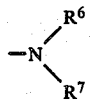

(wherein $R^6$ and $R^7$, which may be the same or different, each represents a hydrogen atom, a lower alkyl group, a hydroxy lower alkyl group, a lower alkoxy lower alkyl group, a cycloalkyl group, an aryl group, an amino lower alkyl group, or an acyloxy lower alkyl group; said $R^6$ and $R^7$ may combine with each other to form a 5- or 6-membered cyclic group which may contain an oxygen atom, a sulfur atom, or a nitrogen atom together with the nitrogen atom bonded thereto) and a salt thereof.

The invention also relates to a process of producing 4-substituted-2-azetidinone compounds shown by the foregoing general formula (I) or a salt thereof, which comprises reacting a carboxylic acid represented by general formula (II)

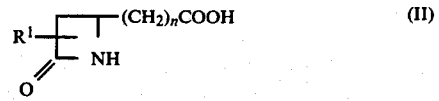

wherein $R^1$ and n have the same meaning as in general formula (I) or a reactive derivative thereof and an amine represented by general formula (VI)

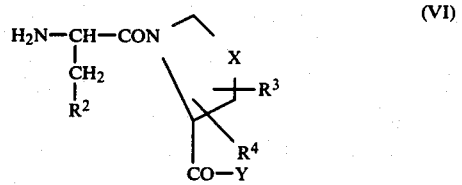

wherein $R^2$, $R^3$, $R^4$, X, and Y have the same meaning as in general formula (I); when Y in the foregoing explanation is a hydroxy group or $R^6$ or $R^7$ represents a hydroxy lower alkyl group or an amino lower alkyl group, these groups may have a protective group or a reactive derivative thereof and, when the reaction product has a protective group, removing the group.

Furthermore, the invention relates to a process of producing a 4-substituted-2-azetidinone compound shown by the foregoing general formula (I) or a salt thereof, which comprises reacting a carboxylic acid represented by general formula (IV)

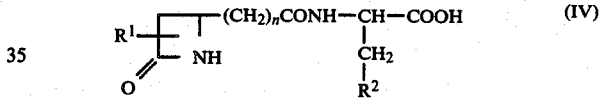

wherein $R^1$, n, and $R^2$ have the same meaning as described above or a reactive derivative thereof and an amine represented by general formula (V)

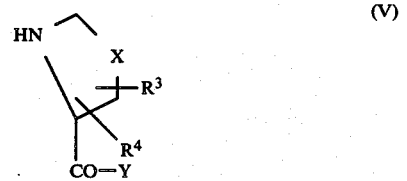

wherein $R^3$, $R^4$, X and Y have the same meaning as described above and when Y is a hydroxy group or $R^6$ or $R^7$ is a hydroxy lower alkyl group or an amino lower alkyl group in the foregoing definition of Y, these groups may have a protective group or a reactive derivative thereof and, when the reaction product has a protective group, removing the protective group.

The lower alkyl group shown by $R^1$, $R^3$, $R^4$, $R^5$, $R^6$ and $R^7$ in the foregoing general formulae includes straight chain or branched alkyl groups each having 1 to 5, preferably 1 to 3 carbon atoms, such as a methyl group, an ethyl group, a propyl group, an isopropyl group, a butyl group, a pentyl group, etc. When both $R^3$ and $R^4$ are a lower alkyl group, these lower alkyl groups can bond to a same carbon atom.

The aromatic acyl group shown by $R^5$ is an unsubstituted or substituted benzoyl or benzenesulfonyl group and the substituent is a straight chain or branched alkyl group having 1 to 5, preferably 1 to 3 carbon atoms, such as a methyl group, an ethyl group, a propyl group, an isopropyl group, a butyl group, a pentyl group, etc.

The aryl group shown by $R^5$ is an unsubstituted or substituted phenyl group. The substituent of the phenyl group is, for example, a nitro group and the phenyl group may have 1 to 3 such substituents.

The lower alkoxy group shown by Y includes straight chain or branched lower alkoxy groups having 1 to 5 carbon atoms, such as a methoxy group, an ethoxy group, a propoxy group, an isopropoxy group, a butoxy group, a tert-butoxy group, a pentyloxy group, etc.

The aralkoxy group shown by Y includes phenyl lower alkoxy groups such as a benzyloxy group, a phenetyloxy group, a 3-phenylpropyloxy group, an α-methylphenetyloxy group

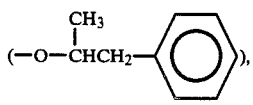

etc.

The hydroxy lower alkyl group shown by $R^6$ and $R^7$ includes lower alkyl groups having 1 to 5 carbon atoms substituted by a hydroxy group, such as a 2-hydroxyethyl group, a 2-hydroxypropyl group

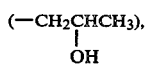

a 4-hydroxybutyl group (—CH₂CH₂CH₂OH), etc.

The lower alkoxy lower alkyl group shown by $R^6$ and $R^7$ includes the foregoing hydroxy lower alkyl groups the hydrogen atom of the hydroxy group of which is substituted by a lower alkyl group having 1 to 5 carbon atoms.

The cycloalkyl group shown by $R^6$ and $R^7$ is cycloalkyl groups having 5 to 10 carbon atoms, which may be crosslinked, such as a cyclopentyl group, a cyclohexyl group, an adamantyl group, etc.

The aryl group shown by $R^6$ and $R^7$ includes aromatic hydrocarbon groups such as phenyl group, a naphthyl group, etc.

The amino lower alkyl group shown by $R^6$ and $R^7$ is straight chain or branched alkyl groups of 1 to 5 carbon atoms having an unsubstituted amino group or a substituted amino group (e.g., a methyl amino group, an ethylamino group, a dimethylamino group, an ethylmethylamino group, a pyrrolidinyl group, a piperidinyl group, a 2-ketopiperidino group

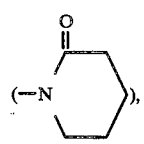

a 2-keto-1-pyrrolidinyl group

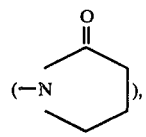

etc.

Also, the acyloxy lower alkyl group shown by $R^6$ and $R^7$ is straight chain or branched alkyl groups of 1 to 5 carbon atoms having a lower acyloxy group, such as an acetyloxy group, a propionyloxy group, an isobutyryloxy group, a butyryloxy group, etc.

$R^6$ and $R^7$ may combine with each other to form a 5- or 6-membered ring group, which may contain an oxygen atom, a sulfur atom or a nitrogen atom, together with the nitrogen atom to which $R^6$ and $R^7$ are bonded as described above and examples of the 5- or 6-membered ring group are a 1-pyrrolidinyl group

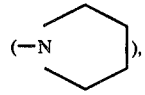

a piperidino group

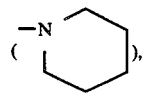

an oxazolidine-3-yl group

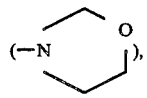

a thiazolidine-3-yl group

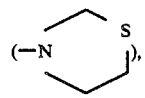

a 2-pyrazolidinyl group

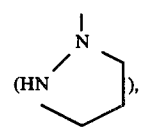

a morpholino group

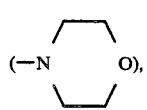

a thiomorpholino group

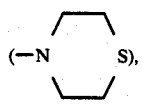

a 1-piperazinyl group

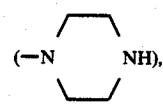

etc.

The desired compound shown by general formula (I) of this invention has at least 3 asymmeteric carbon atoms and there are stereoisomers. Thus, the desired compound of this invention includes each such separated isomer and a mixture of the isomers.

The desired compound of this invention shown by general formula (I) may form a salt with an acid or a base. The salt of the compound included in this invention includes the salts thereof with nontoxic acids (e.g., an inorganic acid salt such as a hydrochloride, a sulfate, etc., and an organic acid salt such as a citrate, an acetate, a tartarate, etc.), and the salts thereof with nontoxic bases (e.g., the salt with an inorganic base, such as a sodium salt, a potassium salt, etc., and the salt with an organic base, such as an ammonium salt, a trimethylamine salt, etc.).

As a compound having relation to the desired compound of this invention shown by formula (I), there is known L-pyroglutamyl-L-histidyl-L-prolinamide (pGlu-His-Pro-$NH_2$) called as "Thyrotropin Releasing Hormone" (TRH).

The existence of TRH has already been known since the 1960's but the structure thereof was confirmed in 1970 (Endocrinology, 86, 1143(1970)). TRH is said to be a hormone controlling the release of thyrotropin (TSH) in the hypophysis of a mammal. However, by the investigation made after then, it has been clarified that the biological function of the tripeptide TRH is not limited to the control of the release of TSH but TRH widely acts on the central nervous system (CNS), and a field of new investigations has been developed based on the discovery (Science, 178, 417(1972) and Lancet, 2, 999(1972). Thus, it is known that TRH and the derivatives thereof have actions on the CNS, such as the decrease of the continuation time of sleep caused by barbiturates or alcohol, the control of hypothermia by the stimulus of various medicaments, the acceleration of motor activity, the prevention of haloperidol-induced catalepsy, memory enhancing effect, the improvement of anti-psychotic effect, an anti-depressive effect, etc., in addition to the TRH releasing activity (U.S. Pat. Nos. 3,865,934 and 3,932,623). Furthermore, it has been discovered that TRH is useful for improving or treating functional or organic disturbances in the brain, for example, a disturbance of consciousness caused by head injury, brain surgery, cerebro-vascular disorders, brain tumors, etc., in particular, an acute or semiacute disturbance of consciousness (Belgian Pat. No. 839,833).

The development of TRH derivatives showing a weaker TSH releasing activity than TRH or almost no TSH releasing activity and having actions on the CNS the same as or higher than the foregoing actions of TRH has been demanded. Thus, various TRH derivatives were synthesized for the foregoing purpose and the actions to CNS have been further enlarged. As the compounds synthesized for the purpose, there are known a TRH derivative which has a weaker TSH releasing activity than TRH, has a narcotic antagonizing action, an action of increasing spontaneous activity, or a dopamine-like action, and is said to be useful for the improvement or the treatment of sonifacients poisoning, disturbance of consciousness, hyperactive children, schizophrenia, nervous depression, and Parkinson's disease (Japanese Patent Publication (unexamined) No. B 116,465/1977) and a TRH derivative which has action of improving and treating the disturbance of consciousness after an external injury of the head and an action of decreasing the continuation time of sleep by hexobarbital, and is said to be useful for the treatment for a patient having a disturbance of consciousness caused by the organic or functional disturbances in the brain, the treatment for a patient showing senility or mental fatigue, and the treatment for depression state (Japanese Patent Publication (unexamined) No. 59,714/1981).

The compound of this invention has the structural feature in the point that the pyroglutamyl (pGlu) structural moiety of TRH is converted into an azetidinone structure ($\beta$-lactam structure) which has never been employed. As to the medicinal action, the compound of this invention has more remarkably strong CNS actions than TRH and conventionally known TRH derivatives and hence are very useful as medicaments. For example, the compounds of this invention are useful for improving a disturbance of consciousness in schizophrenia, nervous depression, the sequels of cerebro-vascular disorders, a head injury, senile dementia, epilepsy, etc., or improving hypobulia, depressive syndrome, memory loss, etc.

The compounds of this invention shown by general formula (I) can be orally or parenterally administered as it is or as a mixture with a proper phamacologically allowable carrier, excipient, diluent, etc., in the form of powders, granules, tablets, capsules, injections (intravenous, subcutaneous, or intramuscular injections), or suppositories. The dose of the compound of this invention shown by formula (I) differs according to this kind of the compound of formula (I), the age, weight, and symptom of a patient, the manner of administration, etc., but is about 0.001 to 10 mg, preferably 0.01 to 0.1 mg (one dose) in the case of injection and 0.05 to 500 mg, preferably 0.1 to 10 mg (one dose) in the case of oral administration.

The following experiments show the action to a low body temperature by pentobarbitol (Experiment 1), the action to the disturbance of consciousness by a head injury (Experiment 2), and the action to acute toxicity (Experiment 3) about typical compounds in the compounds of this invention shown by formula (I).

EXPERIMENT 1

Pentobarbital-induced hypothermia:

Nine male mice weighing 18 to 22 g were used for each dosage of the test compounds. Mice were given i.v. various doses of TRH or testing compounds 10 min. after pentobarbital (55 mg/kg i.p.). Rectal temperature was measured before pentobarbital dosing and immediately before and 30 min. after the test compounds. Effects of test compounds were evaluated as $ED_{1.5° C.}$, the dose required to reduce by 1.5° C. pentobarbital-hypothermia of control group of mice which received only pentobarbital and saline. The results are shown in Table 1.

EXPERIMENT 2

Disturbance of consciousness induced by concussive head injury:

Nine male mice weighing 18 to 22 g were used for each dosage of the test compounds. An acrylate weight containing lead (20.5 g, 19 mm in both diameter and thickness) was dropped to the head of mice from a 18 cm height. Mice were induced loss of consciousness and they remained motionless for some period. The time from the shock up to the onset of spontaneous movement was recorded as the spontaneous movement time. Test compounds were administered intravenously 10 min. before adding concussive head injury and effects of test compounds were evaluated as $ED_{50\%}$, the dose required to shorten by 50% the spontaneous movement time of control group. The results are shown in Table 1.

TABLE 1

| Test compound | (A)* | (B)* |
| --- | --- | --- |
| $N^\alpha$—[(S)—2-azetidinone-4-carbonyl]-L-histidyl-L-prolinamide (Example 1) | 0.01 | 0.1 |
| $N^\alpha$—[(S)—2-azetidinone-4-carbonyl]-L-histidyl-L-thiazolidine-4-carboxamide (Example 6) | 0.05 | |
| $N^\alpha$—[(S)—2-azetidinone-4-carbonyl]-L-N—(2-hydroxyethyl)-L-prolinamide (Example 4) | | 0.35 |
| $N^\alpha$—[(S)—2-azetidinone-4-carbonyl]-$N^\tau$—methyl-L-histidyl-L-prolinamide (Example 19) | 0.004 | |
| TRH | 0.1 | 2.5 |

(A)* Reversal effect against pentobarbital-hypothermia $ED_{1.5°C.}$ (mg/kg i.v.)
(B)* Onset time of spontaneous movement $ED_{50\%}$ (mg/kg i.v.)

EXPERIMENT 3

Acute toxicity:

An aqueous physiological saline solution of 1493 mg/kg of a test compound, $N^\alpha$-[(S)-2-azetidinone-4-carbonyl]-L-histidyl-L-prolinamide was intravenously administered to one group of nine male mice and they were observed for 24 hours but no example of death was observed. That is, $LD_{50}$ (i.v.) of the compound of this invention was higher than 1493 mg/kg. On the other hand, in the case of administering TRH to mice, $LD_{50}$(i.v.) was 751 mg/kg(i.v.).

The the production process of this invention will be explained in more detail.

The reaction courses for the production processes of this invention are shown by the following schemes:

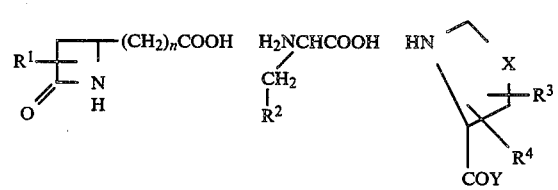

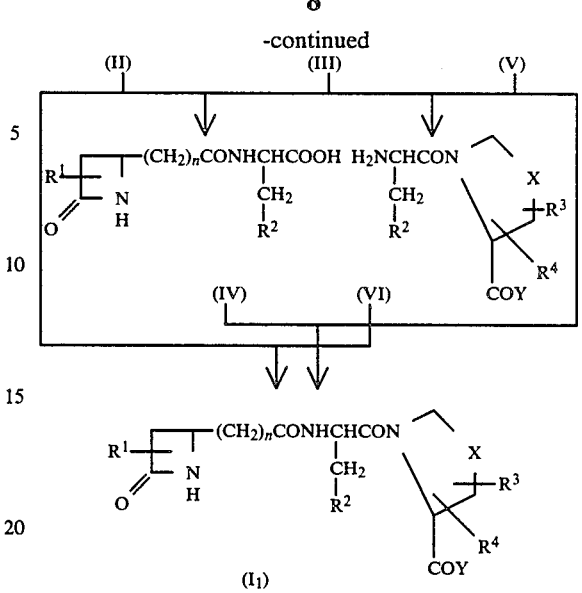

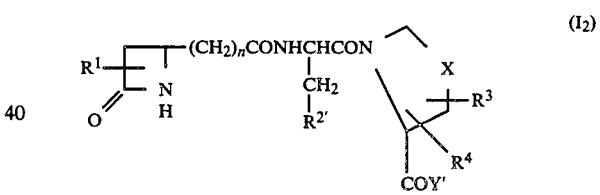

The compounds of this invention shown by above formula ($I_1$) can be converted into the compounds of this invention shown by following formula ($I_2$) by the hydrolysis or the catalytic reduction when Y is an alkoxy group or an aralkoxy group or by the reaction with an unsubstituted or substituted amine when Y is a hydroxy group. Also, when the substituent $R^5$ in the imidazolyl group shown by $R^2$ is an aromatic acyl group or an aryl group, the compound of formula ($I_2$) wherein $R^5$ is hydrogen atom is obtained by removing the substituent by an ordinary manner.

$$(I_2)$$

In the schemes, $R^1$, $R^2$, $R^3$, $R^4$, n, X and Y have the same meaning as described above; $R^{2'}$ represents a case that the substituent $R^5$ in the imidazolyl group shown by $R^{22}$ is a hydrogen atom; and Y' represents a hydroxy group or an unsubstituted or substituted amino group.

That is, according to the process of this invention, the desired compound of formula (I) can be produced (a) by reacting the compound of formula (II) and the compound of formula (III) to form the compound of formula (IV) and then reacting the compound of formula (IV) and the compound of formula (V) or (b) by reacting the compound of formula (III) and compound of formula (V) to form the compound of formula (VI) and then reacting the compound of formula (VI) thus obtained and the compound of formula (II).

Also, the desired compounds of formula ($I_1$) can be induced into the other desired compounds of formula ($I_2$) by converting the substituent Y.

The production reaction for the compounds of formula (I) employed in the foregoing process (a) or (b) is a peptide synthesis reacion and is performed by a known manner. As such a manner usually used, there are a method of using dicyclohexyl carbodiimide as a condensing agent, an azide method, an acid chloride method, an acid anhydride method, an active ester method, etc. These methods are performed as follows: That is, prior to the performance of the peptide forming reaction in each step, the functional groups of the raw material compound, such as an amino group, an imino group, a carboxy group, etc., which do not take part in the reaction, are usually protected and an amino group, an imino group, or a carboxy group of the compound, which takes part in the reaction, is, if necessary, activated. The compound of which the amino group, the imino group or the carboxy group is activated, for example, the active ester may be subjected to the peptide synthesis reaction after once isolated from the reaction mixture or may be subjected to the peptide synthesis reaction without being isolated.

Examples of the protective group for the amino group are a benzyloxycarbonyl group, a t-butyloxycarbonyl group, p-methoxybenzyloxycarbonyl group, a phthaloyl group, a trifluoroacetyl group, etc., and examples of the protective group for the imino group are a tosyl group, a benzyloxycarbonyl group, a p-methoxybenzyloxycarbonyl group, a benzyl group, a 2,4-dinitrophenyl group, etc. Also, the protective group for the carboxy group is used as the form of an ester such as a methyl ester, an ethyl ester, a benzyl ester, a p-nirtobenzyl ester, a t-butyl ester, etc.

The activation of the group which takes part in the reaction is performed by a phosphazo process using phosphorus trichloride, an isocyanate process using phosgene, or a phosphorous acid ester process when the group is an amino group or an imino group or is performed in the form of an active ester (e.g., 2,4-dinitrophenol ester, N-hydroxysuccinimide ester, etc.,), an azide group, or a carboxylic anhydride when the group is a carboxy group.

Among the foregoing methods of performing the peptide synthesis reaction, it is prefered to perform the coupling reactions of the compound of formula (IV) and the compound of formula (V) by the azide method or the method of using dicyclohexyl carbodiimide as the condensing agent. Also, a method of dirctly forming peptide using the N-carboxy anhydride of aminoacid without using a protective group may be employed.

Then, the peptide forming reaction is performed in an inert solvent at room temperature or by heating by an ordinary manner. Examples of the suitable solvent used in the reaction are dimethylformamide (DMF), ethyl acetate, dichloromethane (methylene chloride), tetrahydrofuran, etc.

If it is necessary to remove a protective group from the reaction product, the protective group can be removed by a catalytic reduction when the protective group is benzyl ester; by using anhydrous hydrogen fluoride, N-hydroxy-1,2,3,-benzotriazole (HOBT), or a hydrogen fluoride-pyridine complex when the protective group is p-toluenesulfonyl group; by hydrolysis when the protective group is an alkyl ester; by a catalytic reduction or a hydrobromic acid-acetic acid treatment when the protective group is p-methoxybenzyloxycarbonyl; or an acid decomposition when the protective group is a t-butyloxycarbonyl group.

Furthermore, in the reaction of inducing the desired compound of formula (I) into other desired compound by converting the substituent Y of the compound of formula (I), the reaction conditions maybe suitably selected according to the characters of the compounds taking part in the reaction. The details of these conditions will be explained in the examples.

Furthermore, the invention relates to novel 4-substituted-2-azetidinone compounds shown by general formula (VII)

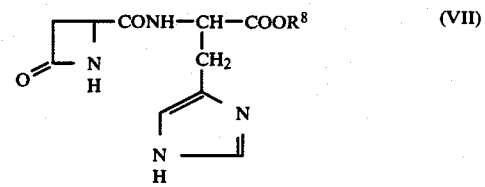

wherein $R^8$ represents a hydrogen atom, a lower alkyl group or an aralkyl group or a salt thereof, and a process of the production thereof.

Examples of the lower alkyl group shown by $R^8$ in the foregoing general formula (VII) are straight chain or branched alkyl groups having 1 to 5, preferably 1 to 3 carbon atoms, such as a methyl group, an ethyl group, a propyl group, a butyl group, a pentyl group, an isopropyl group, etc., and examples of the aralkyl group shown by $R^8$ are aryl lower alkyls such as a benzyl group, a phenetyl group, a naphthylmethyl group, etc.

The novel compound shown by general formula (VII) is useful as an intermediate compound for producing the compound of this invention shown by general formula (I).

The compound shown by general formula (VII) can be produced by reacting a carboxylic acid shown by the formula

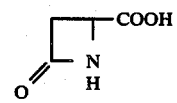

or a reactive derivative thereof and an amine shown by the general formula

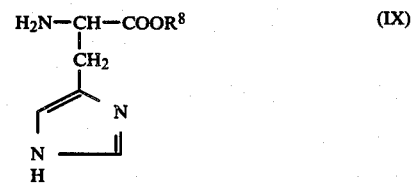

wherein $R^8$ has the same meaning as described above or a reactive derivative thereof. The reaction is a peptide synthesis reaction and can be performed by a known manner as described hereinbefore.

Still further, the invention relates to novel 4-substituted-2-azetidinone compounds represented by the general formula

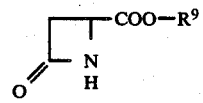

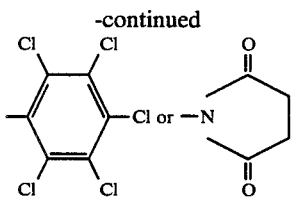

wherein R[9] represents and the production process thereof.

The foregoing compounds of this invention are useful as an intermediate compounds for producing the compound shown by formula (VII) and further is useful as intermediate compounds for producing β-lactam series antibiotics.

The novel intermediate compounds are produced by reacting a carboxylic acid shown by the formula

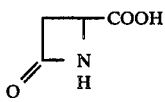

or a reactive derivative thereof and pentachlorophenol or N-hydroxysuccinimide.

The reaction is an ester synthesis reaction and a known esterification method can be suitably selected.

Then, the invention will further explained by the following examples but the examples do not limit the scope of this invention.

In addition, the production processes for the raw materials commonly used in plural examples will first be explained as reference examples.

Also, the abbreviations employed in the examples and the reference examples indicate the following meaning.

TLC: Thin layer chromatography
NMR: Nuclear magnetic resonance spectrum
IR: Infrared absorption spectrum
Mass: Mass analaysis spectrum
Z: Benzyloxycarbonyl
Bn: Benzyl
His: Histidine
Pro: Proline
DNP: 2,4-Dinitrophenyl
Ts: Tosyl
BOC: t-Butyloxycarbonyl
DMF: Dimethylformamide
HOBT: N-Hydroxy-1,2,3-benzotriazole
DCC: Dicyclohexylcarbodiimide
THF: Tetrahydrofuran
HOSu: N-Hydroxysuccinimide
Ph: Phenyl In addition, the compound containing the mark N[im] in the names of the compounds is a mixture of a π nitrogen atom-substituted

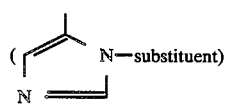

compound of the imidazole ring of histidine and a τ nitrogen atom-substituted

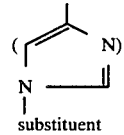

compound.

REFERENCE EXAMPLE 1

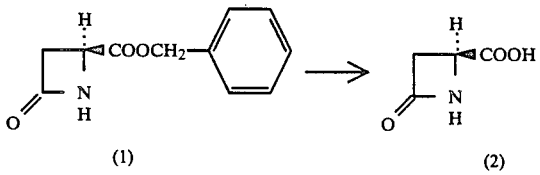

In 350 ml of methanol was dissolved 3.46 g of (S)-4-benzyloxycarbonyl-2-azetidinone (1) and the azetidinone was hydrogenated using 350 mg of 10% palladium-carbon as a catalyst. The catalyst was removed by filtration and the filtrate was concentrated to dryness to provide 1.94 g of (S)-2-azetidinone-4-carboxylic acid (2).

NMR (DMSO-d$_6$) $\delta_{ppm}$: 8.26 (s, 1H), 4.02 (dd, 1H, J=3.4 Hz, 6.9 Hz), 3.21 (dd, 1H, J=6.9 Hz, 16.0 Hz), 2.82 (dd, 1H, J=3.4 Hz, 16.0 Hz).

IR (KBr) cm$^{-1}$: 3320, 1740, 1720.

Mass: 116 (M$^+$+1).

REFERENCE EXAMPLE 2

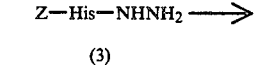

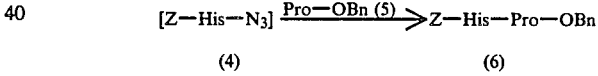

In 99 ml of an aqueous solution of 1N hydrochloric acid was dissolved 10.01 g of N$^\alpha$-benzyloxycarbonyl-L-histidine hydrazide (3). After adding thereto 132 ml of ethyl acetate, 8.25 ml of an aqueous solution of 2.313 g of sodium nitrite was added to the mixture with stirring vigorously under ice-cooling. After performing the reaction at 0° C. for 5 minutes, 39.6 ml of an aqueous 50% potassium carbonate solution was added to the reaction mixture under ice-cooling to alkalify the solution. The reaction mixture was placed in a separation funnel and an organic layer thus formed was collected. Furthermore, the aqueous layer was extracted by 20 ml of ethyl acetate and the extract was combined with the foregoing organic layer. The mixture was dried over anhydrous sodium sulfate under ice-cooling for 10 minutes. By removing anhydrous sodium sulfate by filtration, 152 ml of an ethyl acetate solution of N$^\alpha$-benzyloxycarbonyl-L-histidine azide (4) was obtained. The product was ice-cooled and 20 ml of an ethyl acetate solution of 5.703 g of L-proline benzyl ester (5) was added thereto. The mixture was reacted overnight at 0° C. and then the reaction mixture was concentrated to dryness. The residue was dissolved in 22 ml of chloroform-methanol (10:1) and subjected to silica gel column chromatography. The eluate by chloroform-methanol (95:5)

was concentrated to dryness to provide 6.602 g of N$^\alpha$-benzyloxycarbonyl-L-histidyl-L-proline benzyl ester (6).

NMR (CDCl$_3$) $\delta_{ppm}$: 7.45 (1H), 7.14 (s, 5H), 7.10 (s, 5H), 6.82 (1H), 5.70 (d, 1H, J=8.5 Hz), 5.20 (s, 2H), 5.06 (s, 2H), 4.4–4.8 (m, 2H), 2.8–3.9 (m, 2H), 3.09 (d, 2H, J=5.7 Hz), 1.6–2.5 (m, 4H)

Mass: 476 (M+), 396, 325, 244, 91, 70.

REFERENCE EXAMPLE 3

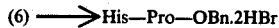

After ice-cooling 20 ml of an acetic acid solution of 25% hydrobromic acid, 1.91 g of compound (6) was added to the solution followed by reaction for 2 hours at 5°–10° C. The reaction mixture was added to 200 ml of dry ether and after quickly removing the precipitates thus formed by filtration and then the reaction mixture was dried overnight in a desiccator with potassium hydroxide, to provide 1.99 g of L-histidyl-L-proline benzyl ester.2-hydrobromide (7).

NMR (CDCl$_3$+CD$_3$OD) $_{ppm}$: 8.75 (1H), 7.57 (1H), 7.35 (s, 5H), 5.2 (1H).

EXAMPLE 1

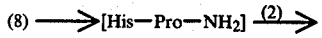

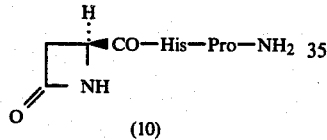

In 13 ml of DMF was dissolved 826 mg of L-histidyl-L-prolinamide 2-hydrobromide (8) and then 2 ml of a DMF solution of 405 mg of triethylamine was added to the solution under ice-cooling. After maintaining 30 minutes under ice-cooling, the precipitates thus formed were filtered off to provide L-histidyl-L-prolinamide (9). The product was immediately used for the subsequent synthesis reaction. In 10 ml of DMF was dissolved 230 mg of compound (2) and then 351 mg of HOBT and 453 mg of DCC were added to the solution under ice-cooling. Then, after stirring the mixture for 15 minutes, the reaction was maintained for 15 minutes at room temperature. The reaction mixture was ice-cooled again and 15 ml of a DMF solution of foregoing compound (9) was added to the reaction mixture followed by reaction overnight at 0° C. The precipitates thus formed were filtered off, the filtrate was concentrated to dryness, the residue was dissolved in 10 ml of chloroform-methanol (4:1) and subjected to silica gel column chromatography. The eluates by chloroform-methanol (7:3) were collected and concentrated to dryness to provide 509 mg of crude N$^\alpha$-[(S)-2-azetidinone-4-carbonyl]-L-histidyl-L-prolinamide (10). When the product was subjected to silica gel column chromatography again and eluted by a mixture of chloroform, methanol, and aqueous ammonia (40:10:1) to provide 394 mg of pure product (10).

NMR (CD$_3$OD) $\delta_{ppm}$: 7.59 (s, 1H), 6,98 (s, 1H), 4.41 (dd, 1H), 4.11 (dd, 1H, J=3.1 Hz, 5.9 Hz), 3.36–3.96 (m, 2H), 3.05 (dd, 1H, J=5.9 Hz, 1.49 Hz), 2.80 (dd, 1H, J=3.1 Hz, 14.9 Hz), 1.72–2.20 (m, 4H).

Mass: 348 (M+), 234, 207, 154, 82, 70, $[\alpha]_D^{23}$=−75.8° (C=0.6, methanol); $[\alpha]_D^{24}$=−100.4° (C=1, water).

When the compound (10) was triturated with a small amount of methanol, the compound crystallized.

M.p. 183°–185° C.

| Elemental analysis for C$_{15}$H$_{20}$N$_6$O$_4$.½H$_2$O: | | | |
|---|---|---|---|
| | C (%) | H (%) | N (%) |
| Calculated: | 50.41 | 5.92 | 23.52 |
| Found: | 50.35 | 6.00 | 23.64 |

When the compound (10) was recrystallized from methanol, the product having a different crystal form was obtained according to the crystallization conditions. For example, products having melting points of 145°–149° C., 154°–157° C., 154°–163° C., 181.5°–183.5° C., 187°–189° C., etc., were obtained and they were confirmed to be polymorphous crystals by infrared absorption spectra (KBr tablet), powder X-ray diffraction, differential scanning calorimetry, etc. The difference in melting point was by the mixing ratio of different crystal forms. The properties (NMR, optical rotation, etc.) of the solution states of these products showed same properties.

EXAMPLE 2

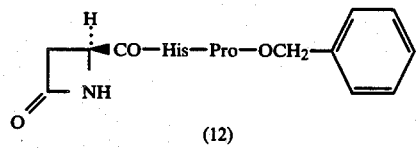

In 45 ml of dichloromethane was dissolved 1.99 g of L-histidyl-L-proline benzyl ester.2-hydrobromide (7) and after cooling the solution to −20° C., 5 ml of a dichloromethane solution of 900 mg of triethylamine was added to the solution. After maintaining the reaction for one hour at −10° C. to −20° C., the precipitates were filtered off to provide a solution containing L-histidyl-L-proline benzyl ester (11). The product was immediately used in the subsequent synthesis reaction.

In 30 ml of dichloromethane was suspended 455 mg of compound (2) and after adding thereto 801 mg of HOBT and 1.059 g of DCC and stirring the mixture for 15 minutes, the reaction was maintained for 15 minutes at room temperature. The reaction mixture was ice-cooled again and then 50 ml of a dichloromethane solution of foregoing compound (11) was added to the reaction mixture. After reacting the mixture for one hour under ice-cooling, the reaction was maintained overnight at room temperature. Precipitates thus formed was filtered off and the filtrate was concentrated to dryness. The residue thus obtained was dissolved in 20 ml of water-methanol (4:1) and subjected to HP-20 column chromatography. When the eluate by water-methanol (1:4) was concentrated to dryness, 1.135 g of crude N$^\alpha$-[(S)-2-azetidinone-4-carbonyl]-L-histidyl-L-proline benzyl ester (12) was obtained. When the product was subjected to silica gel column chromatography again and eluted with chloroform-methanol-aqueous ammonia (40:10:1), 927 mg of the pure product (12) was obtained.

NMR (CD$_3$OD) $\delta_{ppm}$: 7.58 (1H), 7.34 (s, 5H), 6.88 (1H), 5.15 (s, 2H), 4.50 (dd, 1H), 4.08 (dd, 1H, J=3.3 Hz, 5.9 Hz), 3,40–3,92 (m, 2H), 3.04 (dd, 1H, J=5.9 Hz, 14.9 Hz), 2,76 (dd, 1H, J=3.3 Hz, 14.9 Hz), 1.65–2.20 (m, 4H).

Mass: 439 (M+), 325.

EXAMPLE 3

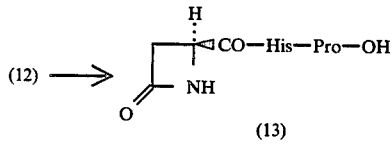

In 150 ml of methanol was dissolved 782 mg of N$^\alpha$-[(S)-2-azetidinone-4-carbonyl]-L-histidyl-L-proline benzyl ester (12) and the compound (12) was hydrogenated for 2 hours at room temperature using 156 mg of 10% palladium-carbon as a catalyst. When the catalyst was filtered off and the filtrate was concentrated, 620 mg of N$^\alpha$-[(S)-2-azetidinone-4-carbonyl]-L-histidyl-L-proline (13) was obtained.

NMR (CD$_3$OD) $\delta_{ppm}$: 8.44 (1H), 7.28 (1H), 4.94 (1H) 4.44 (dd, 1H), 4.14 (dd, 1H, J=3.1 Hz, 5.9 Hz), 3.3–4.0 (m, 2H), 3.25 (dd, 1H, 5.9 Hz, 14.9 Hz), 2.86 (dd, 1H, J=3.1 Hz, 14.9 Hz), 1.7–2.4 (m, 4H).

Mass: (diazomethane treatment, as dimethyl compound): 377 (M+), 263, 221, 96, 70.

EXAMPLE 4

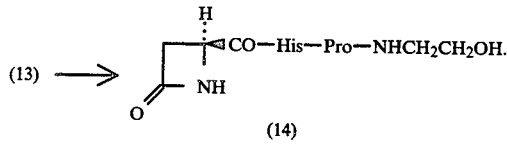

In 8 ml of DMF was dissolved 277 mg of compound (13) and then 168 mg of HOBT and 330 mg of DCC were added to the solution under ice-cooling. After maintaining a reaction for one hour under ice-cooling, the reaction was further maintained for 2 hours at room temperature. After ice-cooling again the reaction mixture, 2 ml of a DMF solution of 80 mg of monoethanolamine to maintain the reaction for one hour and thereafter, the reaction was further maintained overnight at room temperature. The precipitates were filtered off, the filtrate was concentrated to dryness, and the residue thus formed was dissolved in 10 ml of chloroform-methanol-aqueous ammonia (40:10:1) and subjected to silica gel column chromatography. Then, the product was eluted with the same solvent as above to provide 106 mg of N$^\alpha$-[(S)-2-azetidinone-4-carbonyl]-L-histidyl-N-(2-hydroxyethyl)-L-prolinamide (14).

NMR (CD$_3$OD) $\delta_{ppm}$: 7.74 (1H), 7.00 (1H), 4.41 (1H, d,d), 4.12 (d,d, J=2.9 Hz, 5.5 Hz), 3.08 (2H, t, J=7.1 Hz), 3.62 (2H, t, J=7.1 Hz), 2.81 (d,d, J=2.9 Hz, 15.7 Hz).

Mass: 392 (M+), 279, 207.

When the compound (14) was triturated with ether, the compound crystallized. The product was recrystallized from ethanol. M.p. 239°–241° C. (dec.)

[$\alpha$]$_D^{24}$ = −87.3° (C=0.13, methanol).

IR (KBr) cm$^{-1}$: 3280, 3180, 2950, 1760, 1650, 1635, 1550.

| Elemental analysis for C$_{17}$H$_{24}$N$_6$O$_5$: | | | |
|---|---|---|---|
| | C (%) | H (%) | N (%) |
| Calculated: | 52.03 | 6.16 | 21.42 |
| Found: | 51.90 | 6.16 | 21.23 |

EXAMPLE 5

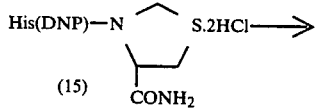

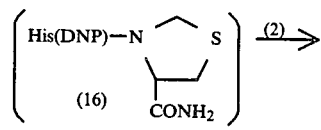

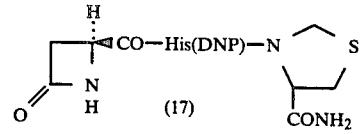

In 30 ml of dichloromethane was dissolved 876 mg of 3-[N$^{im}$-(2,4-dinitrophenyl)-L-histidyl]-L-thiazolidine-4-carboxamide 2-hydrochloride (15) and after adding thereto 2 ml of a dichloromethane solution of 388 mg of triethylamine under ice-cooling, the reaction was performed for 30 minutes at 0° C. to provide a solution of 3-[N$^{im}$-(2,4-dinitrophenyl)-L-histidyl]-L-thiazolidine-4-carboxamide (16).

In 6 ml of DMF was dissolved 223 mg of compound (2) and after adding thereto 389 mg of HOBT and 517 mg of DCC under ice-cooling, the reaction was performed for 30 minutes at 0° C. and then for 30 minutes at room temperature. The reaction mixture was ice-cooled again and 32 ml of the dichloromethane solution of the compound (16) described above was added to the foregoing reaction mixture. The mixture was reacted overnight at 0° C. Precipitates thus formed were filtered off, the filtrate was concentrated to dryness, and the residue was dissolved in 20 ml of chloroform-methanol-aqueous ammonia (40:10:1) and subjected to silica gel column chromatography. The product was eluted with the same solvent as above to provide 347 mg of 3-[N$^\alpha$-[(S)-2-azetidinone-4-carbonyl]-N$^{im}$-(2,4-dinitrophenyl)-L-histidyl]-L-thiazolidine-4-carboxamide (17).

NMR (CD$_3$OD) $\delta_{ppm}$: 8.93 (d, 1H, J=3.1 Hz), 8.63 (dd, 1H, J=3.1 Hz, 9.0 Hz), 7.92 (d, 1H, J=9.0 Hz), 7.87 (s, 1H), 7.26 (s, 1H), 4.43 (d, 2H, J=9.5 Hz), 4.14 (dd, 1H, J=3.1 Hz, 5.9 Hz), 2.86 (dd, 1H, J=3.1 Hz, 14.7 Hz).

Mass: 419 (M+-C$_4$H$_5$N$_2$O$_2$), 372, 248, 81.

EXAMPLE 6

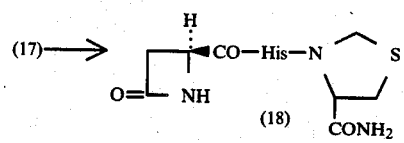

In 15 ml of DMF was dissolved 337 mg of compound (17) and after adding thereto 2 ml of mercapto ethanol, the reaction was maintained for 30 minutes at room temperature. The reaction mixture was concentrated to dryness and the residue was dissolved in 20 ml of chloroform-methanol-aqueous ammonia (30:10:1) and subjected to silica gel column chromatography. Then, the product was eluted with the same solvent as described above to provide 214 mg of 3-[N$^\alpha$-[(S)-2-azetidinone-4-carbonyl]-L-histidyl]-L-thiazolidine-4-carboxamide (18).

NMR (CD$_3$OD) $\delta_{ppm}$: 7.55 (1H), 6.91 (1H), 4.32 (d, 2H, J=9.5 Hz), 4.07 (dd, 1H, J=3.1 Hz, 5.9 Hz).

Mass: 367 (M$^+$+1), 253, 206, 115

REFERENCE EXAMPLE 4

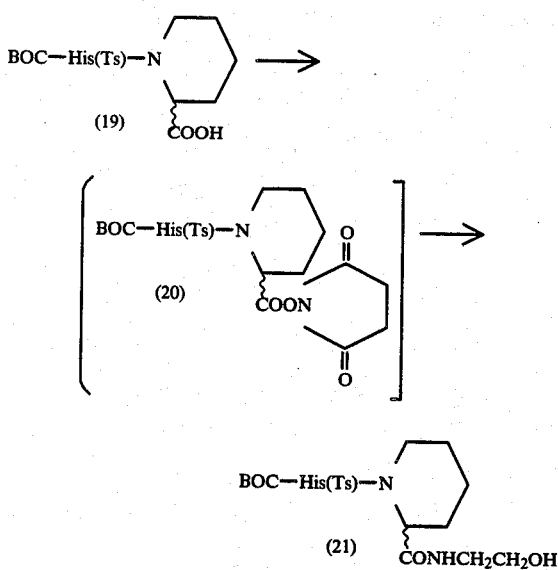

In 90 ml of dry methylene chloride were dissolved 6.28 g of N$^\alpha$-t-butyloxycarbonyl-N$^{im}$-tosyl-L-histidyl-DL-pipecolic acid (19) and 1.39 g of N-hydroxysuccinimide (HOSu) and the solution was cooled in an ice bath. After adding thereto 2.74 g of DCC, the resultant mixture was stirred for 3 hours in an ice bath and after filtering off insoluble matters, the filtrate was concentrated at reduced pressure. The residue thus formed was dissolved in ethyl acetate and the solution was washed successively with an aqueous sodium hydrogencarbonate, water, and aqueous sodium chloride solution. The organic layer thus formed was collected and dried, and then the solvent was removed. The syrupy product thus obtained was triturated with a 1:1 mixture of ether and petroleum ether. The crystalline compound (20) thus obtained was dried and was used in the subsequent reaction as it was. In 40 ml of tetrahydrofuran (THF) was dissolved 2.3 g of the compound (20) and then 5 ml of a THF solution of 251 mg of ethanolamine was added to the solution under ice-cooling. After maintaining the reaction for one hour with stirring under ice-cooling, the solvent was removed under reduced pressure. The residue was dissolved in chloroform and the solution was washed successively with an aqueous sodium hydrogencarbonate solution, water, and an aqueous sodium chloride solution. The organic layer thus formed was collected and after removing therefrom the solvent, the residue thus formed was triturated with ether to provide 1.05 g of solid N$^\alpha$-t-butyloxycarbonyl-N$^{im}$-tosyl-L-histidyl-N-(2-hydroxyethyl)-DL-pipecolamide (21). The mother liquor was concentrated and subjected to silica gel column chromatography. By eluting with 1% methanol-chloroform, 0.66 g of compound (21) was further obtained.

IR (KBr) cm$^{-1}$: 3360, 2920, 1680, 1640, 1170.

NMR (CD$_3$OD) $\delta_{ppm}$: 7.28–8.4 (6H, imidazole ring hydrogen, benzene ring hydrogen), 2.44 (3H, methyl of tosyl group), 1.0–1.5 (broad, BOC hydrogen).

EXAMPLE 7

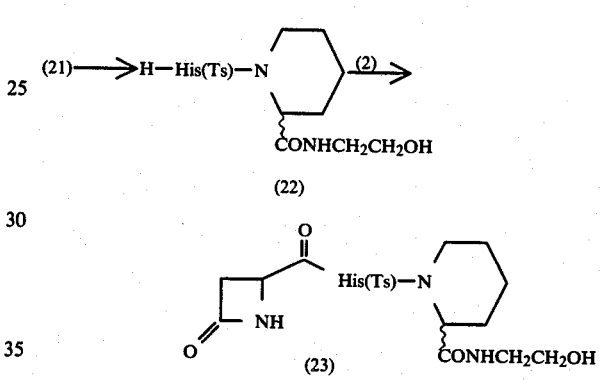

In 40 ml of methylene chloride was dissolved 1.71 g of compound (21) and after adding thereto 40 ml of trifluoroacetic acid under ice-cooling, the reaction was performed for 2 hours with stirring. The reaction mixture thus obtained was dried at reduced pressure, the residue thus formed was azeotropically dehydrated several times using toluene and then dried. By triturating the residue with ether, the solid trifluoroacetate of compound (22) was obtained. The product was dried and used for the subsequent reaction as it was. In 8 ml of DMF was dissolved 1.3 g of the trifluoroacetate and then 274 mg of triethylamine was added to the solution under ice-cooling. Then the pH of the mixture was adjusted to 7 to 8 with additional triethylamine while checking the pH using a pH test paper.

In a mixture of 8 ml of methylene chloride and 1.5 ml of DMF were dissolved 286 mg of compound (2) and 557 mg of DCC to perform the reaction and to the reaction mixture thus obtained was added the foregoing free amine solution under ice-cooling. The reaction mixture thus obtained was stirred overnight in a refrigerator. Insoluble matters were filtered off and the filtrate was concentrated under reduced pressure. The residue was dissolved in chloroform and the solution was washed thrice each time with water. The organic layer thus formed was collected, dried, and then the solvent was removed to provide a syrupy material, which was subjected to column chromatography of 140 ml of silica gel. By eluting with a mixture of 7% methanol-chloroform, 537 mg of the desired compound N$^\alpha$-[(S)-azetidinone-4-carbonyl]-N$^{im}$-toxyl-L-histidyl- N-(2-hydroxyethyl)-DL-pipecolamide (23) was obtained.

NMR (CDCl$_3$) $\delta_{ppm}$: 7.0-8.3 (9H, imidazole hydrogen, benzene hydrogen, NH), 5.08 center (2H, α-methine hydrogen of histidine, α-methine hydrogen of pipecolic acid), 4.08 (1H, 4-position hdyrogen of azetidinone ring), 2.44 (3H, methyl of tosyl group).

Mass m/z: 559 (M-1), 472, 402, 388.

EXAMPLE 8

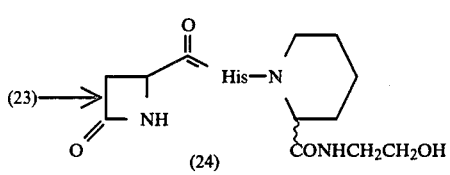

In 15 ml of dry methylene chloride were dissolved 250 mg of compound (23) and 73 mg of HOBT and the reaction was maintained for 5 hours at room temperature with stirring, whereby insoluble matters precipitated. The solvent was removed from the reaction mixture and the residue thus formed was subjected to column chromatography of 100 ml silica gel. By eluting with chloroform-methanol-aqueous ammonia (80:20:2), 116 mg of the desired compound, N$^\alpha$-[(S)-2-azetidinone-4-carbonyl]-L-histidyl-N-(2-hydroxyethyl)-DL-pipecolamide (24) was obtained. The product was a mixture of diastereomers and showed two spots on TLC.

IR (The sample was measured by KBr tablet after lyophilization) cm$^{-1}$: 3250 (NH, OH), 1750 (4-membered ring lactum), 1630 center(broad, amide).

NMR (CD$_3$OD) $\delta_{ppm}$: 7.65 (1H, imidazole ring hydrogen), 6.92 (1H, imidazole hydrogen), 4.14 (1H, d,d, 4-position hydrogen of azetidinone ring), 1.2-1.8 (6H, methylene hydrogen of piperidine ring)

Mass m/z: 406 (M+), 388, 345, 318.

REFERENCE EXAMPLE 5

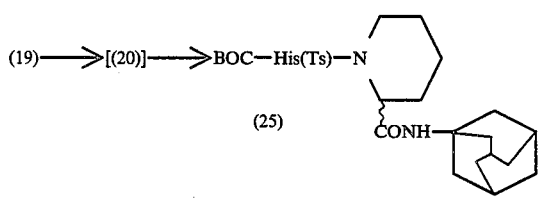

From 2.8 g of the compound (20) prepared from compound (19) by a similar procedure to in Reference example 4 and 755 mg of 1-aminoadamantane, N$^\alpha$-t-butyloxycarbonyl-N$^{im}$-tosyl-L-histidyl-N-(1-adamantyl)-DL-pipecolamide (25) was obtained at a quantitative yield.

NMR (CD$_3$OD) $\delta_{ppm}$: 7.1-8.3 (6H, imidazole ring hydrogen, benzene ring hydrogen), 2.44 (3H, methyl of tosyl group).

Mass: m/z: 653 (M+), 502, 475, 419.

EXAMPLE 9

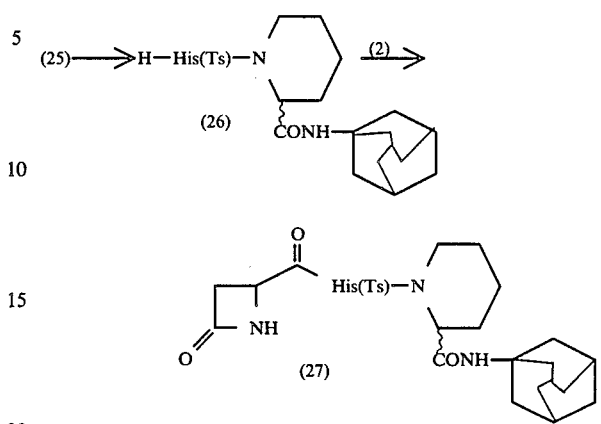

The BOC group was removed from compound (25) by a similar manner to in foregoing Example 7 and the trifluoroacetate of compound (26) thus obtained was converted into the free base using triethylamine as in Example 7. Then, 2.15 m mol the free amine and 290 mg of compound (2) were subjected to a coupling reaction by a similar manner to in Example 7. After the reaction was over, insoluble matters were filtered off and filtrate was concentrated under reduced pressure. The residue thus formed was dissolved in ethyl acetate and the solution was washed thrice each time with water. The organic layer thus formed was collected and dried and after removing the solvent, the residue was subjected to column chromatography of 220 ml of silica gel. By eluting the product with 3% methanol-chloroform, 598 mg of the desired product, N$^\alpha$-[(S)-2-azetidinone-4-carbonyl]-N$^{im}$-tosyl-L-histidyl-N-(1-adamantyl)-DL-pipecolamide (27) was obtained as a powder.

NMR (CD$_3$OD) $\delta_{ppm}$: 7.2-8.24 (6H, imidazole ring hydrogen, benzene ring hydrogen), 4.04 center (1H, 4-position hydrogen of azetidinone ring), 2.44 (3H, methyl of tosyl group), 1.2-2.3 (21H, methylene hydrogen of piperidine ring, adamantyl group hydrogen).

IR (KBr) cm$^{-1}$: 3280, 2900, 1760, 1640 center (broad).

Mass m/z: 650 (M+), 472, 402, 360.

EXAMPLE 10

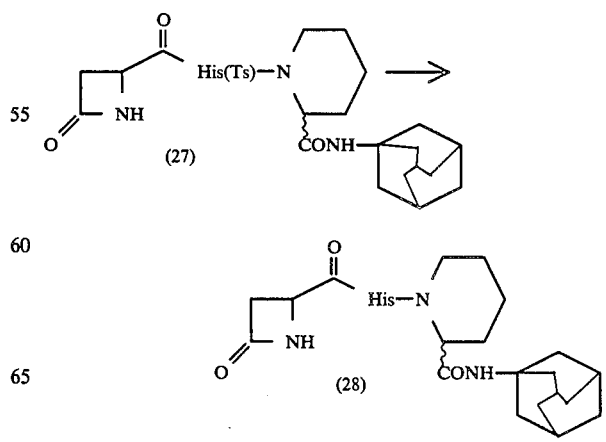

In 10 ml of methylene chloride were dissolved 510 mg of compound (27) and 130 mg of HOBT and the solution was stirred for 7 hours at room temperature. After removing the solvent from the reaction mixture, the residue thus obtained was subjected to silica gel column chromatography. By eluting the product with chloroform-methanol-aqueous ammonia (80:20:2), two kinds of diastereomers were separated. That is, 98 mg of the compound having a small polarity, N$^\alpha$-[2-azetidinone-4-carbonyl]-L-histidyl-N-(1-adamantyl)pipecolamide (28a) was first eluted on the silica gel column and then 128 mg of a mixture of the compound (28a) and the stereoisomer (28b) thereof was obtained. Thereafter, the compound (28b) (63 mg) was eluted. The properties of the compounds (28a) and (28b) are as follows.

Compound (28a):
NMR (CD$_3$OD) $\delta_{ppm}$: 7.66, 7.58, 6.92, 6.90 (imidazole ring C-H), 4.10 (1H, d, d, 4-position hydrogen of azetidinone ring), 2.04 center, 1.72 center (21H, methylene hydrogen of piperidine ring, adamantyl group hydrogen).
IR (KBr) cm$^{-1}$: 3250, 1760, 1610 center (broad), 1520, 1440.
[$\alpha$]$_D^{26}$ = $-74.9°$ (C=1.1, methanol).
Mass m/z: 496 (M+), 382, 345, 318, 261.

Compound (28b):
NMR (CD$_3$OD+DMSO-d$^6$) $\delta_{ppm}$: 7.64, 6.90 (imidazole ring C-H), 4,10 center (1H, d, d, 4-position of azetidinone ring), 2.02 center, 1.70 center (21H, methylene hydrogen of piperidine ring, adamantyl group hydrogen)
IR (KBr) cm$^{-1}$: 3200, 1750, 1530, 1440, 1640.
[$\alpha$]$_D^{26}$ = +82.4° (C=1.3, methanol)
Mass m/z: 496 (M+), 345, 318, 261

REFERENCE EXAMPLE 6

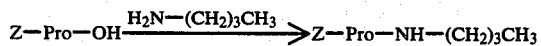

(29)    (30)

In 50 ml of THF was dissolved 4.99 g of N-benzyloxycarbonyl-L-proline and then 2.23 g of triethylamine was added to the solution. Then, after slowly adding thereto 2.39 g of ethyl chloroformate under ice-cooling, the reaction was maintained for one hour at 0° C. to 5° C. Then, 2.19 g of n-butylamine was slowly added to the reaction mixture under ice-cooling, the reaction was further performed for one hour at 0° C. to 5° C. The solvent was removed from the reaction mixture, the residue thus formed was dissolved in ethyl acetate, and the solution was washed successively with an aqueous solution of 1N hydrochloric acid, a saturated aqueous sodium hydrogencarbonate solution, and a saturated aqueous sodium chloride solution. The organic layer this formed was collected, dried by Glauber's salt, and then concentrated to dryness. The product was recrystallized from water to provide 4.31 g of (S)-1-benzyloxycarbonyl-N-butyl-2-pyrrolidinecarboxamide (30). M.p. 88°-90° C.
NMR (CDCl$_3$) $\delta_{ppm}$: 7.36 (s, 5H), 5.17 (s, 2H), 4.33 (dd 1H), 3.51 (t, 2H), 3,21 (dd, 2H), 1.65-2.40 (4H), 1.05-1.65 (4H), 0.70-1.05 (3H).
IR (KBr) cm$^{-1}$: 3280, 2950, 1715, 1640, 1540.
Mass (EI): 304 (M+), 232, 204, 91, 70.

REFERENCE EXAMPLE 7

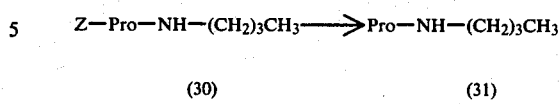

(30)    (31)

In 140 ml of methanol was dissolved 4.41 g of compound (30) and the compound was hydrogenated using 426 mg of 10% palladium-carbon as a catalyst. The catalyst was filtered off and the filtrate was concentrated to provide 2.41 g of (S)-N-butyl-2-pyrrolidinecarboxamide (31).
NMR (CDCl$_3$) $\delta_{ppm}$: 7.3-8.0 (1H), 3.71 (dd, 1H), 2.8-3.4 (4H), 1.1-2.4 (9H), 0.7-1.1 (3H).
IR (neat) cm$^{-1}$: 3280, 2950, 1645, 1520.

REFERENCE EXAMPLE 8

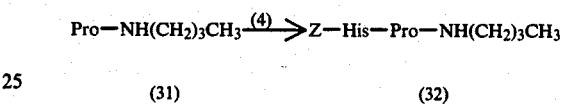

(31)    (32)

To 75 ml of an ethyl acetate solution of N$^\alpha$-benzyloxycarbonyl-L-histidine azide (4) prepared from 4.85 g of N$^\alpha$-benzyloxycarbonyl-L-histidine hydrazide (3) by the method of Reference example 2 was added 2.23 g of compound (31) under ice-cooling and the mixture was placed overnight in a refrigerator to maintain the reaction. The reaction mixture was concentrated and the residue was subjected to silica gel column chromatography. By eluting the product with chloroform-methanol-aqueous ammonia (95:5:0.5), 4.13 g of N$^\alpha$-benzyloxycarbonyl-L-histidyl-N-butyl-L-prolinamide was obtained.
NMR (CDCl$_3$) $\delta_{ppm}$: 7.51 (1H), 7.34 (s, 5H), 6.85, (s, 1H), 5.76 (d, 1H), 5.10 (s, 2H), 4.3-4.8, (2H), 2.8-3.7 (6H), 1.7-2.3 (4H), 1.1-1.7 (4H), 0.7-1.1 (3H).
IR (KBr) cm$^{-1}$: 3250, 2950, 1705, 1635, 1540.
Mass (EI): 441 (M+), 361, 341, 272, 244, 190, 136, 91, 70.

REFERENCE EXAMPLE 9

Z—His—Pro—NH(CH$_2$)$_3$CH$_3$ ⟶

(32)

(33)

To 20 ml of an acetic acid solution of 25% hydrobromic acid was added 1.77 g of compound (32) under ice-cooling and the reaction was maintained for 3 hours at room temperature. The reaction mixture was added to 200 ml of dry ether, the precipitates thus formed were quickly collected by filtration and dried overnight in a desiccator containing potassium hydroxide under reduced pressure to provide 2.14 g of L-histidyl-N-butyl-L-prolinamide.2-hydrobromide (33).

EXAMPLE 11

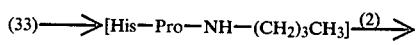

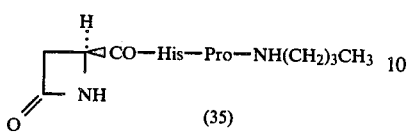

In 10 ml of DMF was dissolved 938 mg of compound (33) and after cooling the solution to −40° C., 415 mg of triethylamine was added to the solution. After reacting for one hour at −30° C. to −40° C., precipitates thus formed were filtered off to provide a DMF solution of L-histidyl-L-butyl-L-prolinamide (34). The product was used for the subsequent synthesis reaction immediately after the formation thereof.

In 5 ml of DMF was dissolved 230 mg of (S)-2-azetidinone-4-carboxylic acid (2) (prepared in Reference example 1) and after adding thereto 406 mg HOBT and 495 mg of DCC under ice-cooling, the reaction was maintained for one hour at 0° C. to 5° C. The reaction mixture was cooled to −40° C. and the DMF solution of the foregoing compound (34) was added to the reaction mixture. The reaction was maintained for 30 minutes at −40° C. and then was further maintained overnight in a refrigerator. Precipitates thus formed were filtered off, the filtrate was concentrated, and the residue thus formed was subjected to silica gel column chromatography. By eluting the product with chloroform-methanol-aqueous ammonia (80:20:2), 471 mg of $N^\alpha$-[(S)-2-azetidinone-4-carbonyl]-L-histidyl-N-butyl-L-prolinamide (35) was obtained.

NMR (D$_2$O, sodium 3-(trimethylsilyl)-1-propanesulfonate) $\delta_{ppm}$: 7.76 (1H, 7.07 (1H), 4.96 (t, 1H), 4.2–4.5 (2H), 2.6–4.0 (8H), 1.7–2.2 (4H), 1.1–1.7 (4H), 0.7–1.1 (3H).

IR (KBr) cm$^{-1}$: 3240, 2950, 1755, 1630, 1540.

Mass (EI): 404 (M+), 305, 290, 235, 207, 165, 110, 70.

$[\alpha]_D^{27} = -81.8°$ (C=0.50, MeOH).

REFERENCE EXAMPLE 10

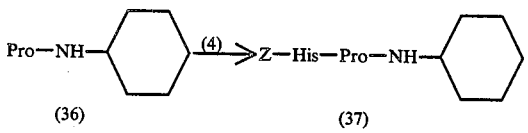

To 30 ml of an ethyl acetate solution of compound (4) prepared from 1.52 g of compound (3) by the method shown in Reference example 2 was added 785 mg of (S)-N-cyclohexyl-2-pyrrolidinecarboxamide (36) prepared by a known method and then the reaction was maintained overnight in a refrigerator. The reaction mixture was concentrated and the residue thus formed was subjected to silica gel column chromatography. By eluting the product with chloroform-methanol-aqueous ammonia (90:10:1), 1.30 g of $N^\alpha$-benzyloxycarbonyl-L-histidyl-N-cyclohexyl-L-prolinamide (37) was obtained.

NMR (CDCl$_3$) $\delta_{ppm}$: 7.54 (s, 1H), 7.32 (s, 5H), 6.88 (s, 1H), 5.77 (d, 1H), 5,09 (s, 2H), 4.61 (dd, 1H), 4.36 (t, 1H), 3.3–4.0 (2H), 2.8–3.3 (3H), 0.9–2.4 (14H).

IR (KBr) cm$^{-1}$: 3250, 2920, 1710, 1630, 1525.

Mass (EI): 467 (M+), 387, 360, 341, 272, 244, 136, 108, 70.

REFERENCE EXAMPLE 11

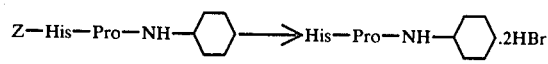

To 15 ml of ice-cooled acetic acid solution of 25% hydrobromic acid was added 1.14 g of compound (37) and the reaction was maintained for 3 hours at room temperature. The reaction mixture thus obtained was added to 150 ml of desiccated ether, the precipitates thus formed were quickly collected by filtration and dried overnight in a desiccator at reduced pressure to provide 1.53 g of L-histidyl-N-cyclohexyl-L-prolinamide.2-hydrobromide.

EXAMPLE 12

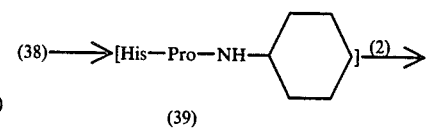

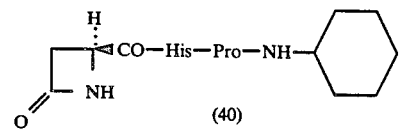

In 10 ml of DMF was dissolved 991 mg of compound (38) and after cooling the solution to −40° C., 415 mg of triethylamine was added to the solution. After maintaining the reaction for one hour at −30° C. to −40° C., precipitates thus formed were filtered off to provide a DMF solution of L-histidyl-N-cyclohexyl-L-prolinamide (39).

In 5 ml of DMF was dissolved 230 mg of compound (2) and after adding thereto 406 mg of HOBT and 495 mg of DCC under ice-cooling, the reaction was maintained for one hour at 0° C. to 5° C. The reaction mixture thus obtained was cooled to −40° C., the foregoing DMF solution of the compound (39) was added to the reaction mixture, and then the reaction was maintained for 30 minutes at −40° C. and then overnight in a refrigerator. Precipitates thus formed were filtered off, the filtrate was concerned, and the residue was subjected to silica gel column chromatography. By eluting the product with chloroform-methanol-aqueous ammonia (80:20:2), 305 mg of $N^\alpha$-[(S)-2-azetidinone-4-carbonyl]-L-histidyl-N-cyclohexyl-L-prolinamide (40) was obtained.

NMR (CD$_3$OD) $\delta_{ppm}$: 7.64 (1H), 6.98 (1H), 4.2–4.5 (1H), 4.12 (dd, 1H), 2.81 (dd, 1H), 0.9–1.2 (14H).

IR (KBr) cm$^{-1}$: 3220, 2920, 1750, 1620, 1540.

Mass (EI): 430 (M+), 316, 235, 180, 152, 99, 70.

$[\alpha]_D^{27} = -69.2°$ C. (C=1.90, MeOH).

REFERENCE EXAMPLE 12

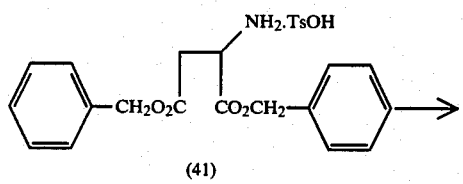

In 1150 ml of ether was suspended 71 g (146.6 m mol) of D-aspartic acid dibenzyl ester p-toluene-sulfonate (41) and while stirring the suspension under ice-cooling (0° C. to 5° C.), 22.5 ml (146.6×1.1 m mol) of triethylamine was added dropwise to the suspension. After stirring the mixture for 2 hours at 0° C. to 5° C., 450 ml of water was added thereto at the same temperature and the mixture was further stirred for 30 minutes. The ether layer thus formed was separated, the aqueous layer was extracted with 200 ml of ether, and the foregoing ether layer was combined with the ether extract. The mixture was washed with 400 ml of a saturated aqueous sodium sulfate solution and dried by anhydrous magnesium sulfate. Ether was distilled off under reduced pressure to provide 45 g of D-aspartic acid dibenzyl ester (42) as a colorless oily product.

REFERENCE EXAMPLE 13

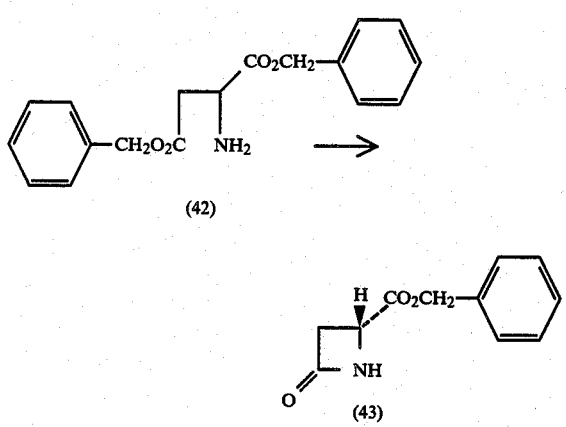

In 485 ml of dry ether was dissolved 45 g (143.8 m mol) of D-aspartic acid dibenzyl ester (42) and after cooling the solution to 0° C. under an argon atmosphere, 20 ml (143.8 m mol) of triethylamine was added dropwise to the solution. Then, 15.6 g (143.9 m mol) of trimethylsilyl chloride was further added dropwise to the mixture at the same temperature as above and the resultant mixture was stirred for one hour. Precipitates thus formed were filtered off under an argon atmosphere and the filtrate was cooled to 0° C. to −5° C. and then 134.8×1.01 m mol of an ether solution of t-butyl magnesium chloride was added dropwise to the mixture with stirring. After further stirring the mixture for 2 hours at 0° C. and then for 3 hours at room temperature, the mixture was cooled to 0° C., 100 ml of 2N HCl (saturated with NH₄Cl) was added to the mixture and after stirring the mixture for 30 minutes, 100 ml of a saturated aqueous ammonium chloride solution was added to the mixture. The ether layer thus formed was separated and the aqueous layer was extracted twice each time with 200 ml of ethyl acetate. The ether layer was combined with the ethyl acetate extract, and after washing the mixture with 300 ml of a saturated aqueous ammonium chloride solution and drying with anhydrous magnesium sulfate, ether and ethyl acetate were distilled off under reduced pressure. To the residue was added 10 ml of ethyl acetate to form crystals, which were collected by filtration to provide 13.7 g of (R)-4-benzyloxycarbonyl-2-azetidinone (43). In addition, the mother liquor was concentrated and purified by silica gel column chromatography (eluant:ethyl acetate-n-hexane (2:1)) to provide 5.1 g of the desired product. M.p. 136°–138° C.

$[\alpha]_D = +33.7°$ (C=1, MeOH).

NMR (DMSO-d⁶) $\delta_{ppm}$: 8.40 (1H, NH), 7.40 (5H, s, phenyl group), 5.20 (2H, s, methylene of benzyl group), 4.22 (1H, d,d, 4-position hydrogen), 3.27 (1H, d,d,d 3-position hydrogen), 2.89 (1H, d,d,d, 3-position hydrogen).

IR (KBr) cm⁻¹: 3200, 1760, 1725, 1280.

REFERENCE EXAMPLE 14

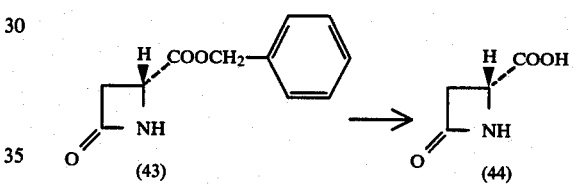

In 250 ml of methanol was dissolved 5 g of compound (43) and the compound was catalytically reduced in the presence of 500 mg of palladium-carbon at normal temperature and normal pressure in a hdyrogen atmosphere. After filtering off the catalyst, methanol was distilled off under reduced pressure. The residue thus formed was crystallized from ether and the crystals thus formed were collected by filtration to provide 2.5 g of the desired product, (R)-2-azetidinone-4-carboxylic acid (44) as the colorless crystals. M.p. 97°–101° C.

NMR (DMSO-d⁶, CD₃OD) $\delta_{ppm}$: 4.60 (1H, d,d, 4-position hydrogen), 3.23 (1H, d,d, 3-position hydrogen), 2.85 (1H, d,d, 3-position hydrogen).

IR (KBr) cm⁻¹: 3310, 1735 (broad), 860.

EXAMPLE 13

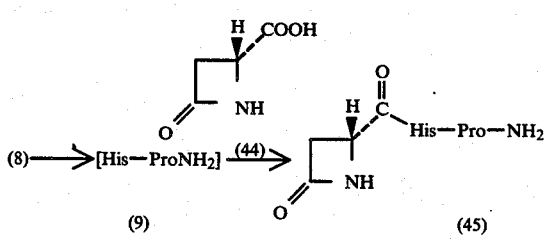

In 13 ml of anhydrous DMF was dissolved 826 mg (2 m mol) of L-histidyl-L-prolinamide 2-hydrobromide (8) followed by cooling to −10° C. To the solution was slowly added 404 mg (2×2 m mol) of triethylamine and the mixture was stirred for 30 minutes at the same temperature. Then, triethylamine hydrobromide thus precipitated was filtered off under an argon atmosphere. The solution was added dropwise to an active ester solution prepared from 230 mg (2 m mol) of (R)-2-azetidinone-4-carboxylic acid (44) (obtained in Reference examples 12 to 14), 351 mg (2×1.3 m mol) of HOBT, 453 mg (2×1.1 m mol) of DCC, and 10 ml of DMF at −20° C. After stirring the mixture for 1.5 hours at the same temperature, the mixture was stirred overnight in a refrigerator. Then, DMF was distilled off from the reaction mixture under reduced pressure, to the residue thus formed was added 10 ml of methylene chloride-methanol-concentrated aqueous ammonia (80:20:2), and crystals thus precipitated were filtered off. The filtrate was subjected to silica gel column chromatography and purified using methylene chloride-methanol-concentrated aqueous ammonia (80:20:2) as the developing solvent to provide 370 mg of $N^\alpha$-[(R)-2-azetidinone-4-carbonyl]-L-histidyl-L-prolinamide (45) as an amorphous powder.

$[\alpha]_D = -21.5°$ (C=1, MeOH).

NMR (D$_2$O) $\delta_{ppm}$: 7.03 (1H, imidazole ring), 6.72 (1H, imidazole ring), 4,95 (1H, m), 4.42 (1H, m) 4,27 (1H, d,d, 4-position hydrogen of azetidinone ring), 3.40–4.00 (2H, m), 3,32 (1H, d,d, 3-position hydrogen of azetidinone ring), 2,74 (1H, d,d, 3-position hydrogen of azetidinone ring), 2.00 (4H, m).

IR (KBr) cm$^{-1}$: 3350, 3150, 1745, 1660, 1625, 1440

Mass: 348 (M+), 304, 278, 234, 207, 190.

EXAMPLE 14

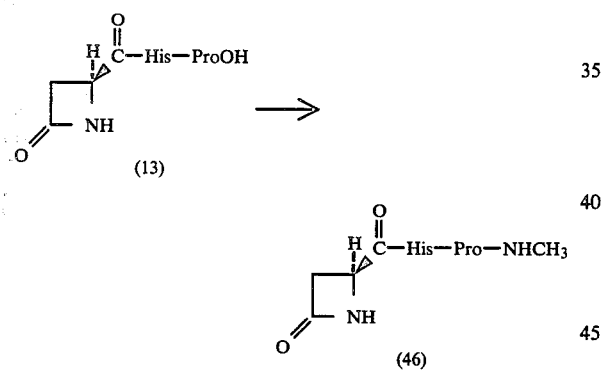

In 2 ml of DMF were dissolved 300 mg of $N^\alpha$-[(S)-2-azetidinone-4-carbonyl]-L-histidyl-L-proline (13) (obtained in Example 3), 116 mg of HOBT, and 177 mg of DCC and after stirring for 7 hours at room temperature, the solution was cooled in an ice bath. Then 0.6 ml of a methanol solution of 30% methylamine was added to the solution and the mixture was reacted overnight with stirring at 2° to 6° C. Insoluble matters were filtered off and the filtrate was concentrated to dryness under reduced pressure. The residue thus formed was purified by column chromatography using LiChroprep Si 60 (size B). By using chloroform-methanol-aqueous ammonia (40:10:1) as the eluant. $N^\alpha$-[(S)-2-azetidinone-4-carbonyl]-L-histidyl-N-methyl-L-prolinamide (46) was obtained. The product was dissolved in water and then lyophilized. The amount of the product thus obtained was 149 mg.

NMR (CD$_3$OD) $\delta_{ppm}$: 7.62 (1H, imidazole ring), 6.94 (1H, imidazole ring), 4.8 (1H, methine group), 4.10 (1H, 4-position hydrogen of azetidinone ring), 2.76 (3H, N-methyl group), 1,6–2.3 (4H, proline ring hydrogen).

IR (KBr) cm$^{-1}$: 3250, 1750, 1630, 1540, 1440.

Mass m/z: 362 (M+), 304, 292, 248, 235, 207.

REFERENCE EXAMPLE 15

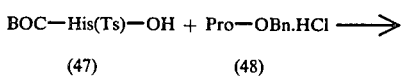

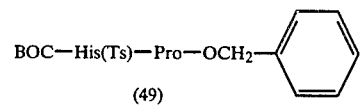

To 100 ml of desiccated methylene chloride were added 10 g of $N^\alpha$-t-butyloxycarbonyl-$N^{im}$-tosyl-L-histidine (47) and 6.50 g of L-proline benzyl ester hydrochloride and the mixture was cooled in an ice bath. After adding thereto 2.72 g of triethylamine, 6.05 g of DCC was further added to the mixture and the resultant mixture was stirred for 30 minutes in an ice-bath and stirred overnight at room temperature. Insoluble matters were filtered off and the filtrate was concentrated. The residue thus formed was purified by silica gel column chromatography. By eluting the product with ethyl acetate-benzene (1:1), 13.5 g of $N^\alpha$-t-butyloxycarbonyl-$N^{im}$-tosyl-L-histidyl-L-proline benzyl ester (49) was obtained.

NMR (CD$_3$OD) $\delta_{ppm}$: 8.14, 7.92, 7.84, 7.40, 7.30 (total 11H, imidazol ring, benzene ring), 5.12 (2H, q, benzyl group), 4.5 center (2H, 2 kinds of methine groups), 2.36 (3H, methyl of tosyl group), 1.30 (9H, t-butyl group).

IR (KBr) cm$^{-1}$: 3400, 3280, 2970, 1740, 1700, 1640, 1590.

Mass m/z: 596 (M+), 523, 480, 364, 290, 155, 91.

REFERENCE EXAMPLE 16

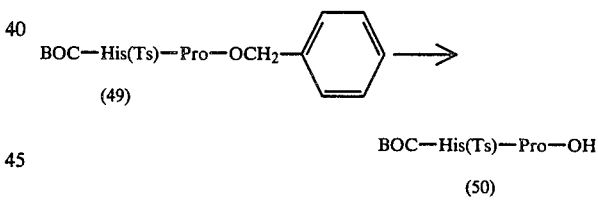

In 150 ml of methanol was dissolved 13.5 g of compound (49) and the compound was catalytically reduced for 5 hours in the presence of 10% palladium-carbon. The catalyst was filtered off and the filtrate was concentrated under reduced pressure. The residue thus formed was dissolved in ethyl acetate and extracted thrice each time with an aqueous sodium hydrogen carbonate solution. The extracts were combined with each other and washed once with ethyl acetate. After acidifying the aqueous layer with 1N hydrochloric acid, the desired compound was extracted with ethyl acetate. Thus, 2.0 g of $N^\alpha$-t-butyloxycarbonyl-$N^{im}$-tosyl-L-histidyl-L-proline (50) was obtained as a foamy product. Also, from the organic layer formed after extracting the product with an aqueous sodium hydrogencarbonate solution, 9.1 g of the starting material (49) was recovered.

The properties of the desired compound (50) thus obtained are shown below.

NMR (CD$_3$OD) $\delta_{ppm}$: 8.16, 7.96, 7.86, 7.46, 7.40, (total 6H, imidazole ring hydrogen, benzene ring hydrogen), 4,48 center (2H, two kinds of methine groups), 2,42 (3H, s, methyl of tosyl group), 1.32 (9H, t-butyl group).

IR (KBr) cm$^{-1}$: 3300, 3100, 2970, 2500–2600, 1710, 1640.

Mass m/z: 388 (M-118), 308, 234.

REFERENCE EXAMPLE 17

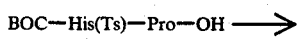

(50)

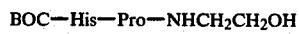

(51)

To 70 ml of methylene chloride were added 3.25 g of compound (50), 0.79 g of monoethanolamine, and 2.61 g of HOBT and the mixture was ice-cooled in an ice-bath. Then, 20 ml of DMF was added to the mixture to form a uniform solution. After further adding 1.99 g of DCC, the mixture was sirred for 2 hours in an ice-bath and then stirred overnight at room temperature. Insoluble matters were filtered off and the filtrate was concentrated under reduced pressure. The residue was dissolved in 70 ml of methylene chloride and after further adding thereto 1.3 g of HOBT, the mixture was stirred again for 20 hours at room temperature. The solvent was distilled off from the reaction mixture under reduced pressure and the residue thus formed was subjected to silica gel column chromatography. By eluting the product with chloroform-methanol-aqueous ammonia (40:10:1), 1.35 g of N$^\alpha$-t-butyloxycarbonyl-L-histidyl-N-(2-hydroxyethyl)-L-prolinamide (51) was obtained.

NMR (CD$_3$OD) $\delta_{ppm}$: 7.64 (1H, imidazole ring), 6.96 (1H, imidazole ring), 4.48 center (2H, two kinds of methine groups), 2.0 center (4H, porline ring), 1.40 (9H, t-butyl group).

IR (KBr) cm$^{-1}$: 3250, 2960, 1700, 1630.

Mass m/z: 395 (M+), 365, 322, 307, 278.

EXAMPLE 15

(51)

(52)

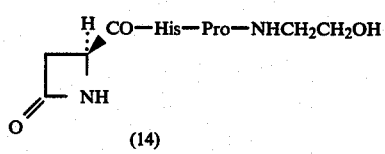

(14)

In 25 ml of methylene chloride was dissolved 790 mg of compound (51) and then 20 ml of trifluoroacetic acid was added dropwise to the solution at 0° C. to 5° C. After stirring the mixture for 2.5 hours in an ice-bath, the reaction mixture was concentrated to dryness under reduced pressure. Furthermore, the product was azeotropically dried several times using toluene and the residue was triturated with dry ether to provide powder of L-histidyl-N-(2-hydroxyethyl)-L-prolinamide.2-trifluoroacetate with a quantitative yield.

In a mixture of 7 ml of DMF and 8 ml of methylene chloride were dissolved 253 mg of compound (2) and 350 mg of HOBT and after adding thereto 530 mg of DCC under ice-cooling, the mixture was stirred for 1.5 hours. To the reaction mixture was added a reaction mixture obtained by neutralizing the foregoing compound (52) in a mixture of 4 ml of DMF and 4 ml of methylene chloride with 445 mg of triethylamine, and the resultant mixture was reacted overnight with stirring in a refrigerator. Insoluble matters were filtered off, the filtrate was concentrated, and the residue was subjected to silica gel column chromatography. By eluting with chloroform-methanol-aqueous ammonia (40:40:1), 313 mg of the compound (14) which was identical with that obtained in Example 4 was obtained.

REFERENCE EXAMPLE 18

(53)

(54)

To an ethyl acetate solution of N$^\alpha$-benzyloxycarbonyl-L-histidinazide (4) prepared from N$^\alpha$-benzyloxycarbonyl-L-histidine hydrazide (3) (6.07 g) by a known method was added 10 ml of a DMF solution of 2.31 g of (S)-N-(2-hydroxyethyl)-2-pyrrolidinecarboxamide (53) under ice-cooling and they were reacted overnight in a refrigerator. The reaction mixture was concentrated and the residue thus formed was subjected to silica gel column chromatography. By eluting the product with chloroform-methanol-aqueous ammonia (90:10:1), 3.43 g of N$^\alpha$-benzyloxycarbonyl-L-histidyl-N-(2-hydroxyethyl)-L-prolinamide (54) was obtained.

NMR (CDCl$_3$) $\delta_{ppm}$: 8.3–8.7 (1H), 7.55 (s, 1H), 7.34 (s, 5H) 6.87 (s, 1H), 5.93 (d, 2H), 5.10 (s, 2H), 4.3–4.8 (2H), 2.8–3.8 (8H), 1.6–2.3 (4H).

Mass (EI): 429 (M+), 341, 272, 244, 136, 108, 79.

REFERENCE EXAMPLE 19

(54)

(55)

To 37.5 ml of ice-cooled acetic acid solution of 25% hydrobromic acid was added 3.22 g of compound (54) and the reaction was maintained for 3 hours at room temperature. The reaction mixture was added to 375 ml of dry ether and the precipitates thus formed were quickly collected by filtration and dried overnight in a desiccator containing potassium hydroxide to provide 4.43 g of L-histidyl-N-(2-acetoxyethyl)-L-prolinamide.2-hydrobromide.

EXAMPLE 16

(55)

(a)

-continued

[His—Pro—NH—CH$_2$CH$_2$OCOCH$_3$] $\xrightarrow{(2)}$ (56)

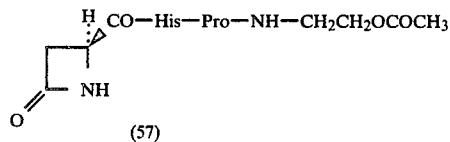

(57)

In 35 ml of DMF was dissolved 4.43 g of compound (55) and after cooling the solution to −40° C., 1.82 g of triethylamine was added to the solution followed by maintaining the reaction for one hour at −30° to −40° C. Then, precipitates thus formed were removed to provide a DMF solution of L-histidyl-N-(2-actoxyethyl)-L-prolinamide (56). The product was immediately used for the subsequent reaction.

In 17.5 ml of DMF was dissolved 863 mg of compound (2) and after adding thereto 1.52 g of HOBT and 1.86 g of DCC, the reaction was maintained for 30 minutes under ice-cooling. The reaction mixture was cooled to −40° C. and after adding thereto the DMF solution of the foregoing compound (56), the reaction was maintained for 30 minutes at −40° C. and then maintained overnight in a refrigerator. Precipitates thus formed were filtered off, the filtrate was concentrated, and the residue thus obtained was subjected to silica gel column chromatography. By eluting the product with chloroform-methanol-aqueous ammonia (80:20:2), 1.60 g of N$^\alpha$-[(S)-2-azetidinone-4-carbonyl]-L-histidyl-N-(2-acetoxyethyl)-L-prolinamide was obtained.

NMR (D$_2$O) $\delta_{ppm}$: 7.74 (s, 1H), 7.05 (1H), 4.93 (t, 1H), 4.1–4.5 (4H), 2.9–3.9 (7H), 2.76 (dd, 1H), 2.7–3.2 (7H).

IR (KBr) cm$^{-1}$: 3230, 2950, 2860, 1755, 1730, 1630, 1540.

Mass (EI): 434 (M$^+$), 364, 320, 262, 235, 154, 70, 43. $[\alpha]_D^{27} = -86.2°$ (C=0.45, MeOH).

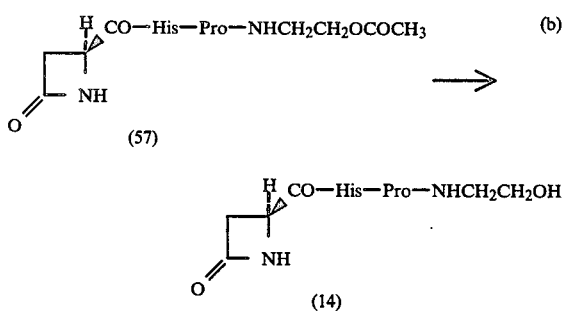

In 12 ml of methanol was dissolved 56 mg of potassium carbonate and after adding thereto 348 mg of compound (57) under ice-cooling, the reaction was maintained for 2 hours under ice-cooling. The reaction mixture thus obtained was subjected to silica gel column chromatography and by eluting the product with chloroform-methanol-aqueous ammonia (80:20:2), 294 mg of N$^\alpha$-[(S)-2-azetidinone-4-carbonyl]-L-histidyl-N-(2-hydroxyethyl)-L-prolinamide was obtained. The physicochemical properties of the product were same as those of the compound (14) obtained in Example 4.

(REFERENCE EXAMPLE 20) EXAMPLE 17-a

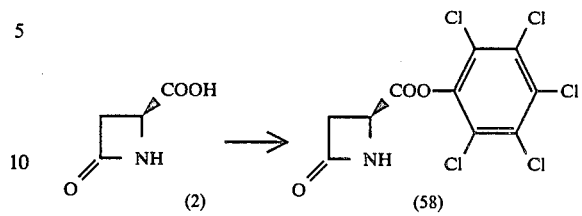

In 200 ml of DMF were dissolved 10 g (8.68 m mol) of (S)-2-azetidinone-4-carboxylic acid (2) and 24.4 g (8.68 m mol) of pentachlorophenol and then 17.93 g (8.70 m mol) of DCC was added to the solution under cooling (0° to 5° C.). After stirring the mixture for 5 hours at room temperature, dicyclohexylurea thus precipitated was filtered off and the filtrate was concentrated under reduced pressure. The residue thus formed was dissolved in 200 ml of ethyl acetate by heating and then cooled. The crystals thus precipitated were collected by filtration to provide 25.6 g of the yellowish crystals of (S)-4-pentachlorophenoxycarbonyl-2-azetidinone (58) having a melting point of 177° to 179° C.

NMR (90 MHz, d$^6$-DMSO-D$_2$O) $\delta_{ppm}$: 3.23 (1H, q, azetidinone ring 3-position), 3.57 (1H, q, azetidinone ring 3-position), 4.70 (1H, q, azetidinone ring 4-position).

Ir (KBr) cm$^{-1}$: 3200, 1775, 1755, 1720.

Mass: 363 (M$^+$), 335, 266, 237.

EXAMPLE 17-b

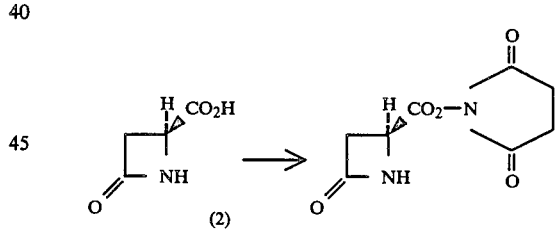

In 20 ml of DMF was dissolved 690 mg of (S)-2-azetidinone-4-carboxylic acid (2) and after adding thereto 690 mg of HOSu and 1.236 g of DCC under ice-cooling, the reaction was performed for 30 minutes under ice-cooling and then for 4 hours at room temperature. Insoluble matters were filtered off from the reaction mixture and then the solvent was distilled off to provide a light-brown solid product. When the product was recrystallized from dioxane-petroleum ether (5:1), 750 mg of (S)-4-(2,5-dioxopyrrolidine-1-yl)-oxycarbonyl-2-azetidinone was obtained.

NMR (DMSO-d$^6$, TMS) $\delta_{ppm}$: 8.70 (broad, 1H), 4.62 (dd, 1H), 3.84 (s, 4H).

IR (KBr) cm$^{-1}$: 3320, 2920, 2840, 1810, 1780, 1750, 1730, 1720, 1650, 1620, 1570

Mass (CI in beam): 213 (M$^+$+1), 185, 171, 116

(REFERENCE EXAMPLE 21) EXAMPLE 17-c

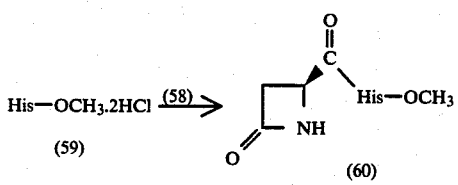

In 75 ml of DMF was suspended 6.05 g (25 m mol) of L-histidine methyl ester 2-hydrochloride (59) and after cooling the suspension to 0° to 5° C., 5.05 g (50 m mol) of triethylamine was slowly added dropwise to the suspension. Thereafter, the mixture was stirred for 15 minutes at the same temperature.

Then, 9.50 g (25 m mol) of compound (58) was added to the mixture as a powder and after stirring the mixture for one hour at the same temperature, the mixture was allowed to stand overnight at room temperature. Triethylamine hydrochloride thus precipitated was filtered off, the filtrate was concentrated under reduced pressure. The residue thus formed was mixed with 40 ml of ethyl acetate and 30 ml of water followed by shaking and then the aqueous layer thus formed was collected. The ethyl acetate layer was extracted twice each time with 20 ml of water. The aqueous layers were combined with each other and water was distilled off under reduced pressure. The residue was mixed with acetonitrile and benzene and the mixture was concentrated under reduced pressure. The residue was crystallized from 30 ml of methanol and the crystals thus formed were collected to provide 4.1 g of the colorless crystals of $N^\alpha$-[(S)-2-azetidinone-4-carbonyl]-L-histidine methyl ester (60) having a melting point of 142° to 147° C.

NMR (90 MHz, d$^6$-DMSO) $\delta_{ppm}$: 2.94 (2H, d, $\beta$-position methylene of histidine group), 3.60 (3H, s, methyl group), 4.02 (1H, q, azetidinone ring 4-position), 4.54 (1H, m, $\alpha$-position methine of histidine group), 6.72 (1H, s, imidazole ring), 7.56 (1H, s, imidazole ring), 8.20 (1H, s, NH), 8.56 (1H, d, azetidinone ring NH).

IR (KBr) cm$^{-1}$: 3250, 3100, 2950, 1770, 1750, 1740, 1720, 1650, 1550.

EXAMPLE 17-d

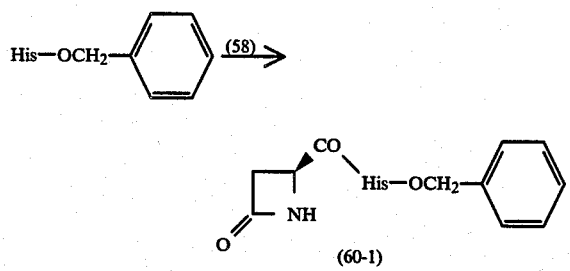

In 20 ml of chloroform was dissolved 1.178 g (2 m mol) of histidine benzyl ester.2-p-toluenesulfonate and then 404 mg (2 m mol) of triethylamine was slowly added to the solution under cooling to 0° C. To the solution was added 766 mg (2 m mol) of (S)-4-pentachlorophenoxycarbonyl-2-azetidinone (58) as a powder and the mixture was stirred overnight at 0° to 5° C. To the reaction mixture was added 30 ml of chloroform and the desired product was extracted twice each time with 30 ml of water. Then, water was distilled off under reduced pressure and the residue thus formed was azeotropically dehydrated with benzene-acetonitrile to provide a colorless sticky product. The product was subjected to silica gel column chromatography using 50 ml Wako gel C-200 and elution with ethyl acetate-methanol-concentrated aqueous ammonia (40:10:0, 470 mg of $N^\alpha$-[(S)-2-azetidinone-4-carbonyl]-L-histidine benzyl ester (60-1) having a melting point of 194° to 199° C. as colorless crystals.

NMR (90 MHz, d$^6$-DMSO) $\delta_{ppm}$: 2.58 (1H, m, azetidinone ring 3-position), 2.96 (2H, d, histidine group $\beta$-position methylene), 3.12 (1H, m, azetidinone ring 3-position), 4.00 (1H, m, azetidinone ring 4-position), 4.62 (1H, m, histidine group $\alpha$-position methine), 5.10 (2H, s, benzyl position), 6.80 (1H, s, imidazole ring), 7.36 (5H, s, benzene ring), 7.56 (1H, s, imidazole ring), 8.20 (1H, s, NH), 8.58 (1H, d, NH).

IR (KBr) cm$^{-1}$: 3260, 2980, 2760, 1750, 1650, 1540

EXAMPLE 17-e

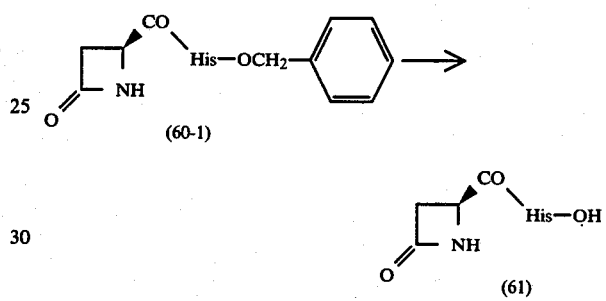

In 20 ml of methanol was suspended 342 mg of compound (60-1) and the compound was catalytically reduced with the addition of 20 mg of 10% palladium-carbon at ambient temperature and ordinary pressure. After the absorption of hydrogen had stopped, the catalyst was filtered off and methanol was distilled off under reduced pressure to provide 230 mg of $N^\alpha$-[(S)-2-azetidinone-4-carbonyl]-L-histidine (61) having a melting point of 213° to 215° C. (dec.) as colorless crystals.

NMR (90 MHz, D$_2$O) $\delta_{ppm}$: 2.80 (1H, q, azetidinone ring 3-position), 3.20 (2H, m, histidine group $\beta$-position), 3.38 (1H, q, azetidinone ring 3-position), 4.28 (1H, q, azetidinone ring 4-position), 4.58 (1H, m, histidine $\alpha$-position methine), 7.30 (1H, s, imidazole ring), 8.60 (1H, s, imidazole ring).

IR (KBr) cm$^{-1}$: 3400, 3260, 2560, 1750, 1630, 1570, 1390.

EXAMPLE 17-A

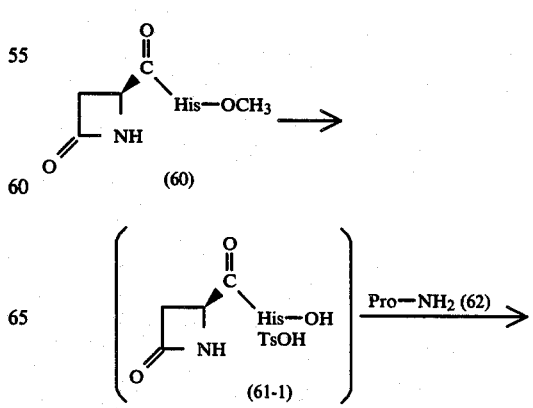

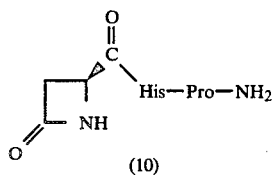

After cooling 20 ml of an aqueous solution of 0.1N sodium hydroxide to 0° to 5° C., 532 mg (2 m mol) of compound (60) was added thereto and the mixture was stirred for 1.5 hours at the same temperature. Then, 760 mg (4 m mol) of p-toluenesulfonic acid monohydrate was added to the mixture at the same temperature and water was distilled off under reduced pressure. The residue thus obtained was azeotropically dehydrated with acetonitrile and benzene and then dried under reduced pressure. The powder obtained was dissolved in 20 ml of DMF and after adding thereto 228 mg (2 m mol) of L-prolinamide (62) and 412 mg (2 m mol) of DCC, the mixture was stirred overnight at room temperature. Dicyclohexylurea thus precipitated was filtered off, the filtrate was concentrated under reduced pressure, and the residue thus formed was dissolved in 20 ml of water. After filtering off insoluble matters, water was distilled off under reduced pressure. After drying the residue thus formed under reduced pressure, the residue was dissolved in 7 ml of methanol by heating and after stirring the solution under cooling, crystals thus precipitated were collected by filtration to provide 500 mg of the colorless crystals of $N^\alpha$-[(S)-2-azetidinone-4-carbonyl]-L-histidyl-L-prolinamide having a melting point of 179° to 184° C. The physicochemical properties of the product were same as those of the compound (10) obtained in Example 1.

EXAMPLE 17-B

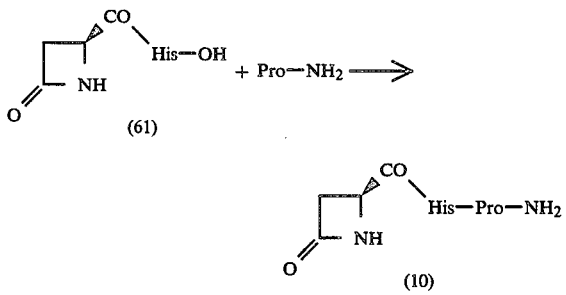

In 10 ml of DMF was suspended 252 mg (1 m mol) of compound (61) and after adding thereto 115 mg (1 m mol) of N-hydroxysuccinimide and then 114 mg (1 m mol) of prolinamide and 206 mg (1 m mole) of DCC under cooling to 0° C., the resultant mixture was allowed to stand overnight at 0° to 5° C. and then stirred for 2 days at room temperature. After filtering off the crystals thus precipitated, DMF was distilled off under reduced pressure. The residue formed was mixed with 5 ml of water and after filtering off insoluble matters, water was distilled off under reduced pressure. After azeotropically dehydrating the residue with the addition of benzene-acetonitrile, 3 ml of methanol was added to the residue and the mixture was stirred to provide 82 mg of the crystals of $N^\alpha$-[(S)-2-azetidinone-4-carbonyl]-L-histidyl-L-prolinamide (10). The physicochemical properties of the product were same as those of the product obtained in Example 17-A.

EXAMPLE 18

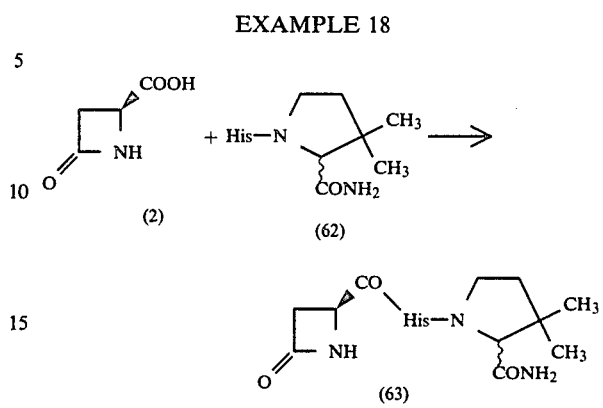

In a mixture of 2 ml of DMF and 10 ml of methylene chloride were dissolved 211 mg of (S)-2-azetidinone-4-carboxylic acid (2) and 248 mg of HOBT and the solution was ice-cooled. After adding thereto 472 mg of DCC, the mixture was stirred for one hour at room temperature. Then, a 10 ml of a DMF solution of 426 mg of L-histidyl-DL-(3,3-dimethyl)prolinamide (62) was added to the mixture and the resultant mixture was stirred for 2 days at 0° to 4° C. Insoluble matters were collected by filtration and washed with DMF. The filtrate was combined with the washings and the solvent was distilled off from the mixture under reduced pressure. The residue was subjected to column chromatography of 150 ml of silica gel. By eluting with chloroform-methanol-aqueous ammonia (80:20:2), $N^\alpha$-[(S)-2-azetidinone-4-carbonyl]-L-histidyl-DL-(3,3-dimethyl)-prolinamide (63) was obtained. The aqueous solution was lyophilized to provide 63 mg of a white powder. The product was a mixture of diastereomers showing two spots on TLC.

IR (KBr) cm$^{-1}$: 3250 (broad), 1750, 1670, 1630, 1540, 1440.

NMR (CD$_3$-OD) $\delta_{ppm}$: 7.64, 6.96, 6.88 (2H, imidazole ring), 4.14 (1H, d,d, azetidinone ring 4-position), 1.80 center (2H, proline ring), 1.06, 1.12, 1.06, 0.92 (6H, proline ring 3-position dimethyl).

Mass m/z: 376 (M+), 343, 316, 306, 262, 98.

Reference example 22 (starting materials for Examples 19 and 22)

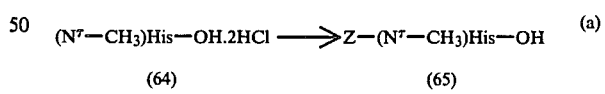

In 130 ml of water was dissolved 9.9 g of L-N$^\tau$-methyl-histidine.2-hydrochloride (64) and the solution was cooled in an ice-sodium chloride cooling bath. The pH of the solution was adjusted to 11 by the addition of an aqueous solution of 2N sodium hydroxide and while maintaining the inner temperature at 0° to 5° C., 10.5 g of carbobenzoxy chloride was added dropwise to the mixture. During the operation, the pH of the system was controlled to 11 to 12 by the addition of an aqueous solution of 2N sodium hydroxide. Thereafter, the mixture was stirred for one hour at 0° to 5° C. while keeping the pH thereof at 12±0.5 by adding occasionally an aqueous solution of 2N sodium hydroxide. After the change in pH had stopped, the solution was further stirred for 1.5 hours at 5° to 10° C. The reaction mixture was washed twice each time with ethyl acetate, the aqueous solution thus formed was collected, and the pH of the solution was adjusted to 3.9 with 4N hydrochloric acid. Then, the pH thereof was adjusted to 2.2 by the addition of 2N p-toluenesulfonic acid. The reaction mixture was saturated with sodium chloride and extracted four times with acetonitrile-isobutanol-ethyl acetate (1:1:2). The organic layer thus obtained was concentrated under reduced pressure and the residue was triturated with acetonitrile. After filtering off insoluble matters, the filtrate was concentrated to provide a yellow syrupy product. The product was subjected to column chromatography using 600 ml of silica gel and by eluting the product with chloroform-methanol-aqueous ammonia (60:40:3), 8.8 g of $N^\alpha$-benzyloxycarbonyl-$N^\tau$-methyl-L-histidine (65) was obtained as a foamy material.

IR (KBr) cm$^{-1}$: 3100 center (broad), 1700, 1590, 1390.

NMR (CD$_3$OD) $\delta_{ppm}$: 7.86 (1H, imidazole ring), 7.32 (5H, benzene ring), 6.96 (1H, imidazole ring), 5.04 (2H, benzyl 4.30 center (1H, d,d, methine group), 3.68 (3H, N-methyl).

$[\alpha]_D^{25} = +22.2°$ (C=1, methanol).

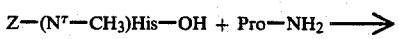

(65)

Z—(N$^\tau$—CH$_3$)His—Pro—NH$_2$ (66)

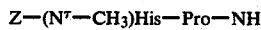

In 25 ml of dry DMF were dissolved 1.65 g of compound (65) and 621 mg of L-prolinamide and the solution was cooled to 5° to 10° C. Then, 1.03 g of p-toluenesulfonic acid and 1.35 g of DCC were added to the solution and the mixture was allowed to stand overnight in a refrigerator. Insoluble matters were filtered off, the filtrate was concentrated under reduced pressure, and the the residue was triturated with a mixture of ethyl acetate and ether. Then, 3.2 g of the insoluble matters was subjected to column chromatography of 500 ml of silica gel and by eluting using chloroform-methanol-aqueous ammonia (80:20:2), 2.0 g of $N^\alpha$-benzyloxycarbonyl-$N^\tau$-methyl-L-histidyl-L-prolinamide (66) was obtained.

IR (KBr) cm$^{-1}$: 3300 center(broad), 1620-1720 (broad), 1510, 1440.

NMR (CD$_3$OD) $\delta_{ppm}$: 7.48 (1H, imidazole ring), 7.32 (5H, benzene ring), 6.90 (1H, imidazole ring), 5.04 (2H, benzyl 3.64 (3H, N-methyl), 2.0 center(4H, proline ring).

Mass (FD) m/z: 399 (M+).

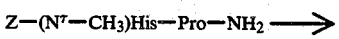

(66)

(N$^\tau$—CH$_3$)His—Pro—NH$_2$.2HBr (67)

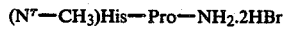

To 24 ml of an acetic acid solution of 25% hydrobromic acid was added 2.04 g of compound (66) and the mixture was stirred for 1.5 hours at room temperature. The reaction mixture was poured in 260 ml of dry ether and white precipitates thus formed were collected by filtration. The precipitates were dried over potassium hydroxide under reduced pressure to provide 2.2 g of a hygroscopic solid of N$^\tau$-methyl-L-histidyl-L-prolinamide.2-hydrobromide (67).

EXAMPLE 19

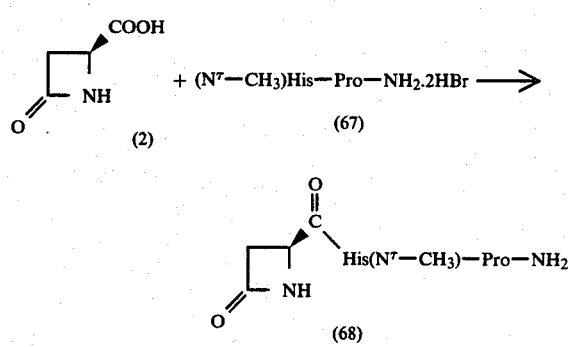

In a mixture of 7 ml of DMF and 7 ml of methylene chloride were dissolved 323 mg of compound (2) and 380 mg of HOBT and after ice-cooling the solution, 579 mg of DCC was added to the solution, whereby crystals precipitated soon. After stirring for about 20 minutes, a solution of the free amine compound prepared from 1.0 g of compound (67) and 521 mg of triethylamine in DMF under ice-cooling was added to the reaction mixture. The reaction mixture thus obtained was stirred for 20 hours in a refrigerator, insoluble matters were filtered off, and the filtrate was concentrated to provide a syrupy residue. The residue was subjected to silica gel column chromatography and by eluting with chloroform-methanol-aqueous ammonia (80:20:2), 543 mg of $N^\alpha$-[(s)-2-azetidinone-4-carbonyl]-N$^\tau$-methyl-L-histidyl-L-prolinamide (68) was obtained.

IR (KBr) cm$^{-1}$: 3250, 1750, 1670, 1630.

NMR (CD$_3$OD) $\delta_{ppm}$: 7.52 (1H, imidazole ring), 6.96 (1H, imidazole ring), 4.44 center (1H, m, methine hydrogen), 4.12 center (1H, d,d, azetidinone ring 4-position hydrogen), 3.70 (3H, s, N-methyl), 2.0 center (4H, proline ring)

Mass m/z: 362 (M+), 319, 292, 249, 221.

$[\alpha]_D^{25} = -68.6°$ (C=1, methanol)

REFERENCE EXAMPLE 23 (RAW MATERIAL FOR EXAMPLE 20)

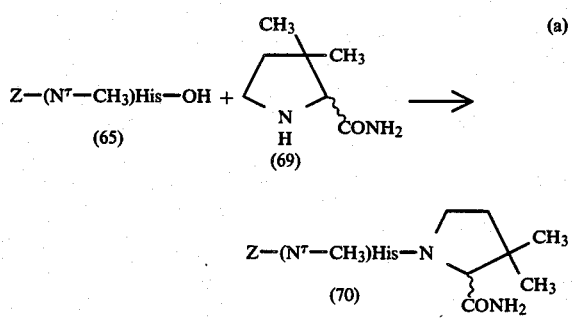

By reacting 2.24 g of compound (65) and 1.05 g of 3,3-dimethyl-DL-prolinamide (69) in a similar method to that in Reference example 22 b), 3.2 g of $N^\alpha$-benzyloxycarbonyl-N$^\tau$-methyl-L-histidyl-3,3-dimethyl-DL-prolinamide (70) was obtained, which was a mixture of diastereomers.

NMR (CD₃OD) $\delta_{ppm}$: 7.52, 7.48 (1H, imidazole ring), 7.32 (5H, benzene ring), 6.88, 6.84 (1H, imidazole ring), 5.04 (2H, benzyl), 3.64, 3.60 (3H, N-methyl).

IR (KBr) cm⁻¹: 3300, 2920, 1620–1720(broad).

Mass m/z: 427 (M⁺), 383, 319, 286, 277, 258.

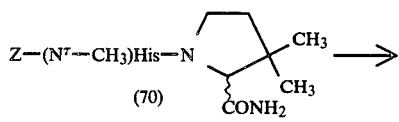

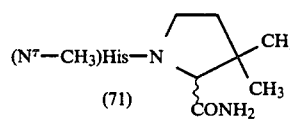

By following the procedure described in Reference example 22 c), N^τ-methyl-L-histidyl-3,3-dimethyl-DL-prolinamide·2-hydrobromide (71) was obtained with a quantitative yield from 3.2 g of compound (70). The product was used for the subsequent reaction as it was.

EXAMPLE 20

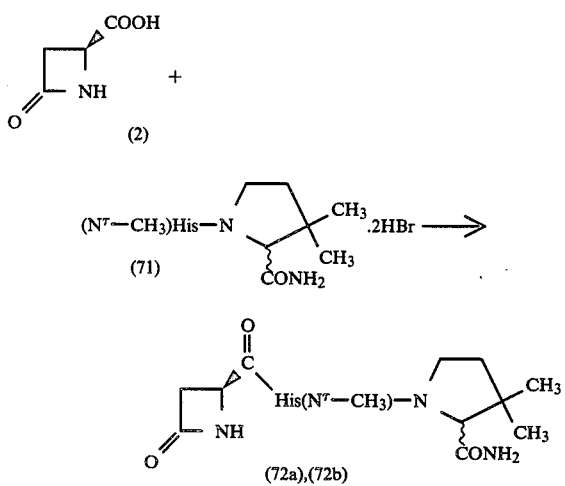

By following a similar manner to that in Example 19, 329 mg of compound (2) was reacted with 1.3 g of compound (71) and the reaction product thus obtained was subjected to silica gel column chromatography. The product was eluted with chloroform-methanol-aqueous ammonia (80:20:2). The desired reaction product, N^α-[(S)-2-azetidinone-4-carbonyl]-N^τ-methyl-L-histidyl-3,3-dimethyl-DL-prolinamide was a mixture of a diastereomer (72a) having a weak polarity on chromatograph and a diastereomer (72b) having a strong polarity. The product first eluted was 244 mg of a mixture of (72a) and (72b) in a ratio of 8:2, the product eluted in the next was 254 mg of a mixture of (72a) and (72b) of 1:1, and the product finally eluted was 182 mg of a mixture of (72a) and (72b) of 2:8.

Properties of the diastereomer having weak polarity [ratio of (72a) and (72b)=8:2]

IR (KBr) cm⁻¹: 3250 center (broad), 1750, 1670, 1630, 1540, 1510, 1440.

NMR (CD₃OD) $\delta_{ppm}$: 7.50 (1H, imidazole ring), 6,92 (1H, imidazole ring), 4.8 (1H, methine), 4.10 (1H, d, d, azetidinone 4-position hydrogen), 4.0 (1H, methine), 3,66 (3H, N-methyl), 1.12, (1.08 (6H, two kinds of methyl).

Mass m/z: 390 (M⁺), 373, 347, 320, 278, 249, 221.

$[\alpha]_D^{27} = -27.3°$ (C=1, methanol).

Properties of the diastereomer having strong polarity [ratio of (72a) and (72b)=2:8]

IR (KBr) cm⁻¹: 3250 (broad), 1750, 1670, 1630, 1440.

NMR (CD₃OD) $\delta_{ppm}$: 7.56 1H, imidazole ring), 6.90 (1H, imidazole ring), 4.14 (1H, d,d, azetidinone ring 4-position hydrogen), 3.68 (3H, N-methyl), 1.08, 0.92 (6H, two kinds of methyl.

Mass m/z: 390 (M⁺), 347, 320, 277, 249, 221.

$[\alpha]_D^{27} = -7.9°$ (C=1, methanol).

REFERENCE EXAMPLE 24 (RAW MATERIAL FOR EXAMPLE 21)

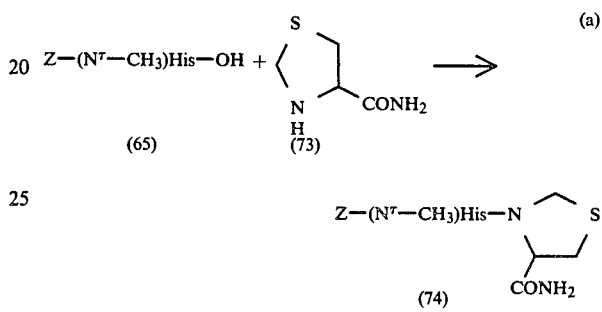

By reacting 2.25 g of compound (65) and 0.89 g of L-thiazolidine-4-carboxamide (73) in a similar manner to that in Reference example 22(b), 1.72 g of 3-[N^α-benzyloxycarbonyl-N^τ-methyl-L-histidyl]-L-thiazolidine-4-carboxamide (74) was obtained as a foamy material.

IR (KBr) cm⁻¹: 3270, 1640–1720 (broad), 1510, 1410, 1250.

NMR (CD₃OD) $\delta_{ppm}$: 7.48 (1H, imidazole ring), 7.32 (5H, benzene ring), 6.90 (1H, imidazole ring), 5.06 (2H, benzyl 3.64 (3H, N-methyl).

Mass m/z: 417 (M⁺), 373, 346, 286, 258.

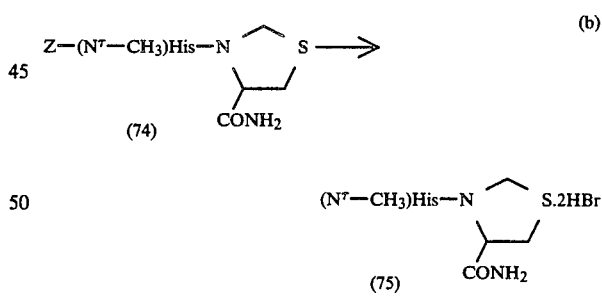

By following the procedure described in Reference example 22 c), 1.9 g of 3-[N^τ-methyl-L-histidyl]-L-thiazolidine-4-carboxamide·2-hydrobromide (75) was obtained from 1.70 g of compound (74). The product was used for the subsequent reaction as it was.

EXAMPLE 21

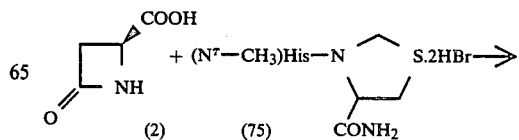

-continued

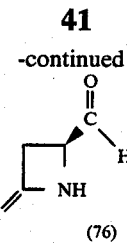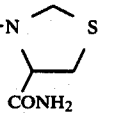
(76)

By following the procedure described in Example 19, 416 mg of 3-[N$^\alpha$-[(S)-2-azetidinone-4-carbonyl]-N$^\tau$-methyl-L-histidyl]-L-thiazolidine-4-carboxamide (76) was obtained as a foamy material from 230 mg of compound (2) and 900 mg of compound (75).

IR (KBr) cm$^{-1}$: 3250, 1750, 1630–1680 (broad), 1420.

NMR (CD$_3$OD) $\delta_{ppm}$: 7.46 (1H, imidazole ring), 6.90 (1M, imidazole ring), 4.9 center (3H, methine, methylene), 4.4 (1H, methine), 4.10 (1H, d,d, azetidinone ring 4-position hydrogen), 3.64 (3H, N-methyl).

Mass m/z: 381 (M+), 326, 309, 281, 267, 249

EXAMPLE 22

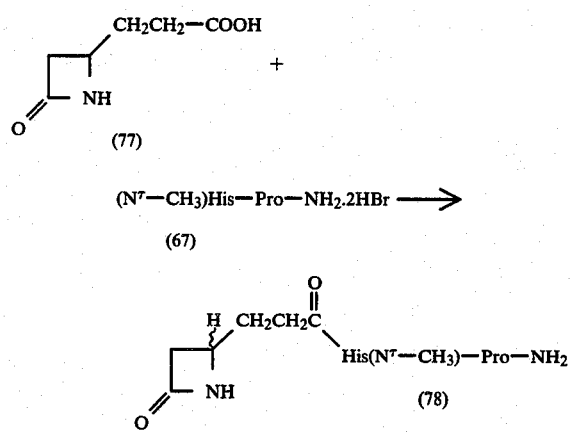

By performing a similar reaction to that in Example 19 using 413 mg of DL-4-(2-carboxyethyl)-2-azetidinone (77) and 1.12 g of compound (67), 540 mg of N$^\alpha$-[(RS)-3-(2-oxo-4-azetidinyl)propionyl]-N$^\tau$-methyl-L-histidyl-L-prolinamide (78) was obtained. The product was a mixture of diastereomers.

IR (KBr) cm$^{-1}$: 3250, 1730, 1660, 1630, 1540, 1510, 1440.

NMR (CD$_3$OD) $\delta_{ppm}$: 7.52 (1H, imidazole ring), 6.96 (1H, imidazole ring), 4.80 (1H, methine), 4.44 (1H, methine), 3,68 (3H, N-methyl), 3,3-3.96 (3H, azetidinone ring 4-position hydrogen), proline ring), 1.94 center (4H, proline ring).

Mass m/z: 390 (M+), 348, 320, 307, 277, 249.

REFERENCE EXAMPLE 25 (RAW MATERIAL FOR EXAMPLE 23)

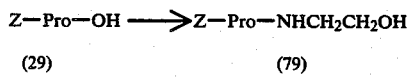 (a)

In 40 ml of THF were dissolved 9.96 g of N-benzyloxycarbonyl-L-proline (29) and 4.45 g of triethylamine and the solution was ice-cooled. Then, 6.10 g of ethyl chloroformate was slowly added to the solution under ice-cooling and then a solution of 5.13 g of monoethanolamine in THF (15 ml) was added to the mixture.

The reaction mixture thus obtained was stirred for 15 minutes under ice-cooling and then stirred for 1.5 hours at room temperature. After distilling off THF under reduced pressure, 150 ml of ethyl acetate and 50 ml of water were added to the residue and the organic layer thus formed was separated from the aqueous layer.

The organic layer was washed in succession with an aqueous solution of 1N hydrochloric acid, an aqueous solution of 0.1N aqueous hydroxide, water, and then an aqueous sodium chloride solution. After drying the organic layer, the solvent was removed, whereby precipitating crystals, which were collected by filtration and recrystallized from ethyl acetate to provide 5.23 g of (S)-1-benzyloxycarbonyl-N-2-hydroxyethyl-2-pyrrolidinecarboxamide (79).

M.p. 104°–106° C.

IR (KBr) cm$^1$: 3420, 3270, 1680, 1640, 1540.

NMR (CDCl$_3$) $\delta_{ppm}$: 7.36 (5H, s, benzene ring), 5.16 (2H, q, benzyl 4.30 (1H, t, methine 2.04 center (5H, proline ring, OH).

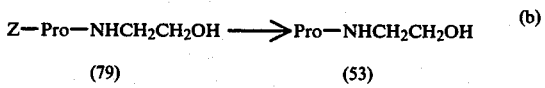 (b)

In 70 ml of methanol was dissolved 5.92 g of compound (79) and the compound was catalytically reduced by an ordinary method using 10% palladium-carbon as a catalyst. After the reaction, the catalyst and the solvent were removed to provide 3.2 g of syrupy (S)-N-2-hydroxyethyl-2-pyrrolidinecarboxamide (53). The product was solidified when it was refrigerated.

NMR (CD$_3$OD) $\delta_{ppm}$: 2.96–3.84 (7H, proline ring, hydroxyethyl), 1.64–2.36 (4H, proline ring).

IR (neat) cm$^{-1}$: 3250, 1640 (broad), 1530 (broad)

Mass m/z: 159 (M+1), 127, 70.

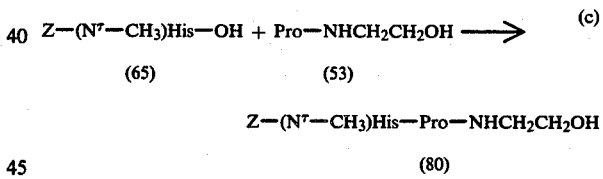 (c)

In 25 ml of dry DMF were dissolved 1.54 g of N$^\alpha$-benzyloxycarbonyl-N$^\tau$-methyl-L-histidine (65) and 0.80 g of compound (53) and the solution was ice-cooled.

After adding 1.01 g of p-toluenesulfonic acid monohydrate to the solution, 1.36 g of DCC was also added to the mixture. The mixture was stirred overnight in a refrigerator to perform the reaction. Thereafter, the reaction mixture was stirred for 1.5 hours at room temperature. After filtering off insoluble matters, the filtrate was concentrated under reduced pressure, the residue thus formed was subjected to column chromatography of 300 ml of silica gel, and the product was eluted with chloroform-methanol-aqueous ammonia (80:20:2) to provide 1.7 g of N$^\alpha$-benzyloxycarbonyl-N$^\tau$-methyl-L-histidyl-N-2-hydroxyethyl-L-prolinamide (80) as a foamy material.

NMR (CD$_3$OD) $\alpha_{ppm}$: 7.54 (1H, imidazole ring), 7.32 (5H, benzene ring), 6.92 (1H, imidazole ring), 5.04 (2H, benzyl 3.64 (3H, N-methyl), 2.0 center (4H, proline ring).

Mass m/z: 443 (M+), 413, 355, 286, 250

IR (neat) cm$^{-1}$: 3250 (broad), 1620–1720 (broad)

Z—(N$^\tau$—CH$_3$)His—Pro—NHCH$_2$CH$_2$OH ⟶ (d)

(80)

(N$^\tau$—CH$_3$)His—Pro—NHCH$_2$CH$_2$O$\overset{\overset{O}{\|}}{C}$CH$_3$·2HBr (81)

To 22 ml of an acetic acid solution of 25% hydrobromic acid was added 1.7 g of compound (80) and the reaction was maintained for 1.5 hours at room temperature. The reaction mixture was added to 250 ml of dry ether to form white precipitates. The precipitates were collected by filtration and dried under reduced pressure to provide N$^\tau$-methyl-L-histidyl-N-2-acetoxyethyl-L-prolinamide-2-hydrobromide (81) with a quantitative yield. The product was used for the subsequent reaction as it was.

Example 23

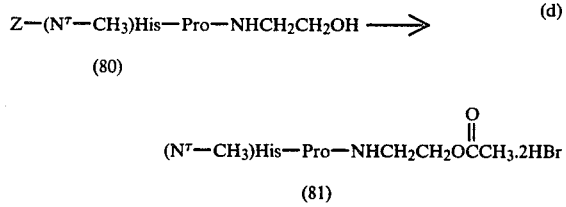

(2)

(N$^\tau$—CH$_3$)His—Pro—NHCH$_2$CH$_2$O$\overset{\overset{O}{\|}}{C}$CH$_3$·2HBr ⟶

(81)

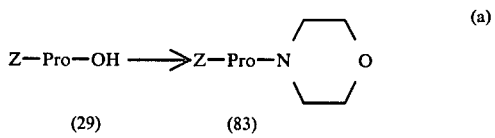

(82)

In a mixture of 7 ml of methylene chloride and 7 ml of DMF were dissolved 317 mg of compound (2) and 448 mg of HOBT and the solution was ice-cooled. Then, after adding thereto 683 mg of DCC, the mixture was stirred for 20 minutes under ice-cooling. To the reaction mixture was added a free amine solution prepared by reacting 1.37 g of compound (81) and 670 mg of triethylamine in 12 ml of DMF under ice-cooling followed by filtration. The mixture was stirred for 38 hours in a refrigerator to complete the reaction. Insoluble matters were filtered off, the filtrate was dried under reduced pressure, and the residue was subjected to column chromatography using 300 ml of silica gel. By eluting the product with chloroform-methanol-aqueous ammonia (85:15:2), 593 mg of N$^\alpha$-[(S)-azetidinone-4-carbonyl]-N$^\tau$-methyl-L-histidyl-N-2-acetoxyethyl-L-prolinamide (82) was obtained as foamy material. The product was dissolved in water and then lyophilized.

IR (KRr) cm$^{-1}$: 3250, 1750, 1730, 1640, 1540, 1230.

NMR (CD$_3$OD) $\delta_{ppm}$: 7.56 (1H, imidazole ring), 6.96 (1H, imidazole ring), 4.80 (1H, methine hydrogen), 4.40 (1H, methine hydrogen), 4.16 center (3H, azetidinone ring 4-position hydrogen), —C$\underline{H}_2$O—$\overset{\overset{O}{\|}}{C}$CH$_3$), 2.0 center (7H, proline ring, acetyl).

Mass (FD) m/z: 449 (M+1).

REFERENCE EXAMPLE 26 (RAW MATERIAL FOR EXAMPLE 24)

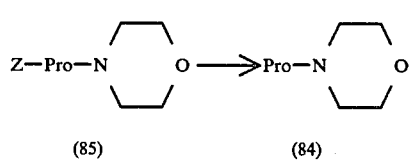

(29)　　　(83)

In 80 ml of dry tetrahydrofuran were dissolved 4.9 g (20 m mol) of Z-proline (29) and 3.5 g (26 m mol) of HOBT and then 4.53 g (22 m mol) of DCC was slowly added to the solution at 0° C. After stirring the mixture for 30 minutes at the same temperature, a solution of 1.74 g (20 m mol) of morpholine dissolved in 20 ml of dry DMF was gradually added dropwise to the mixture. The resultant mixture was allowed to stand for 18 hours at room temperature and then the solvent was distilled off under reduced pressure. The residue thus formed was dissolved in 200 ml of ethyl acetate and the solution was washed, in succession, with 75 ml of an aqueous solution of 0.5N hydrochloric acid, 75 ml of a saturated aqueous solution of sodium hydrogen carbonate, and then 50 ml of water. After drying the solution with anhydrous magnesium sulfate, ethyl acetate was distilled off and the residue thus formed was purified by silica gel column chromatography (490 ml of Wako Gel C-200; ethyl acetate as a eluent) to provide 5.0 g of N-[N-benzyloxycarbonyl-L-prolyl]morpholine (83) having a melting point of 139°-140° C.

NMR: 90 MHz (CDCl$_3$) $\delta_{ppm}$: 1.70-2.40 (m, 4H, proline ring), 3.20-4.00 (m, 10H, proline ring, morpholine ring), 4.40-4.90 (m, 1H, proline ring methine), 5.10, 5.14 (q, q, 2H, benzyl), 7.32, 7.34 (s, s, 5H, benzene ring)

IR (KBr) cm$^{-1}$: 2960, 2910, 2860, 2830, 1680, 1635.

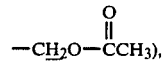

Z—Pro—N◯O ⟶ Pro—N◯O

(85)　　　(84)

In 100 ml of ethanol was suspended 4.9 g of compound (83) and after adding thereto 250 mg of 10% palladium carbon, the mixture was stirred for 4 hours in a hydrogen stream. After filtering off 10% palladium-carbon, ethanol was distilled off under reduced pressure from the filtrate to provide 2.8 g of crude N-(L-prolyl)-morpholine (84).

NMR: 90 MHz (CDCl$_3$) $\delta_{ppm}$: 1.40-2.30 (m, 4H, proline ring), 2.60-3.40 (m, 2H, proline ring), 2.97 (s, 1H), 3.40-4.10 (m, 9H, morpholine ring).

IR (neat) cm$^{-1}$: 3280, 2960, 2840, 1635.

Mass: 185 (M+1), 142, 114, 98, 70, 43.

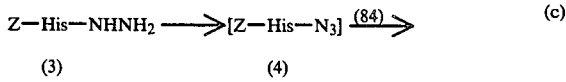

(3)　　　(4)

45

-continued

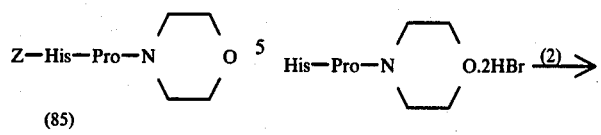

(85)

In 54 ml of an aqueous solution of 1N hydrochloric acid was dissolved 5.46 g (18 m mol) of L-Z-histidine hydrazide (3) and after adding thereto 72 ml of ethyl acetate, the mixture was cooled to 0° C. Then, 5.4 ml of an aqueous solution of 4N-NaNO₂ was added to the mixture at the same temperature followed by stirring for 5 minutes and after adding thereto 21.6 ml of an aqueous solution of 50% potassium carbonate followed by stirring vigorously, the ethyl acetate layer thus formed was separated. The aqueous layer was extracted with 18 ml of cooled ethyl acetate, the ethyl acetate extract was combined with the foregoing ethyl acetate layer, and the mixture was dried with anhydrous sodium sulfate for 5 minutes with stirring under ice-cooling. After filtering off sodium sulfate, the filtrate was cooled to −20° C. and after slowly adding dropwise a solution of 2.76 g (15 m mol) of compound (84) dissolved in 10 ml of ethyl acetate to the filtrate, the mixture was allowed to stand overnight in a refrigerator at 4° C. After allowing to raise the temperature to room temperature, ethyl acetate was distilled off under reduced pressure and the residue thus formed was purified by silica gel column chromatography (600 ml of Wako gel C 200, chloroform-methanol-aqueous ammonia (10:1:0.1)) to provide 6.46 g of N-[N$^\alpha$-benzyloxycarbonyl-L-histidyl-L-prolyl]morpholine (85) as a colorless oil.

NMR: 90 MHz (CDCl₃) $\delta_{ppm}$: 1.60–2.40 (m, 4H, proline ring), 3.80 (d, 2H, methylene of His moiety), 3.20–4.00 (m, 10H, morpholine ring, proline ring), 4.40–5.00 (m, 2H, methine) 5.08 (s, 2H, benzyl), 6.09 (m, 1H, amide), 6.86 (s, 1H, imidazole ring), 7.12 (s, 5H, benzene ring), 7.52 (s, 1H, imidazole ring)

IR (KBr) cm⁻¹: 3250, 2950, 2840, 1710, 1640, 1630.
Mass: 455 (M+), 374, 341, 305, 272, 244.

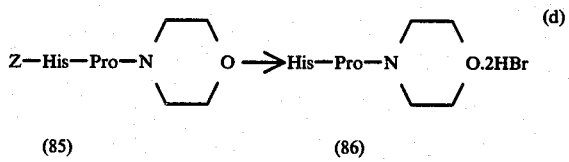

In 21.4 ml of acetic acid was dissolved 6.46 g (14.2 m mol) of compound (85) and after adding thereto 42.8 g of an acetic acid solution of 25% hydrobromic acid under ice-cooling, the mixture was stirred for 1.5 hours. After the reaction mixture was added 600 ml of desicated ether, precipitates were filtered to provide 6.50 g of the crude crystals of N-[L-histidyl-L-prolyl]morpholine.2-hydrobromide (86).

46

EXAMPLE 24

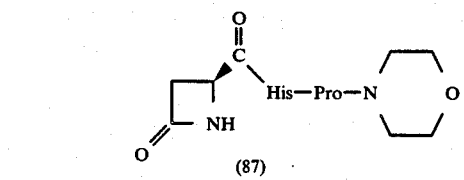

[SOLUTION A]

In 10 ml of dry DMF was dissolved 230 mg (2 m mol) of compound (2) and after adding thereto, in succesion, 351 mg of HOBT and 453 mg of DCC with stirring under cooling to 0°, the mixture was stirred for 40 minutes at the same temperature.

[SOLUTION B]

In 13 ml of dry DMF was dissolved 966 mg (2 m mol) of compound (86) and the solution was cooled to −15° C. After adding thereto 404 mg of triethylamine with stirring, the mixture was stirred for 30 minutes at the same temperature and then triethylamine hydrobromide was filtered off udner cooling.

To solution A cooled to 0° C. was added solution B cooled to −15° C. and after stirring the mixture for 2 hours at −10° C., the mixture was allowed to stand overnight in a refrigerator at 4° C.

After raising the temperature of the reaction mixture to room temperature, insoluble matters were filtered off, DMF was distilled off under reduced pressure, and the residue thus obtained was purified by silica gel column chromatography (400 ml of Wako gel C-200 chloroform-methanol-aqueous ammonia (40:10:1)) to provide 480 mg of the colorless crystals of the desired product, 4-[N$^\alpha$-[(S)-2-azetidinone-4-carbonyl]-L-histidyl-L-prolyl]morpholine (87) having a melting point of 148°–150° C.

NMR: 90 MHz (CD₃OD) $\delta_{ppm}$: 1.60–2.40 (m, 4H, proline ring), 2.72 (d, d, 1H, azetidinone ring 3-position), 4.11 (d, d, 1H, azetidinone ring 4-position), 6.96 (s, 1H, imidazole ring), 7.63 (s, 1H, imidazole ring).

IR (KBr) cm⁻¹: 3200, 3040, 2850, 1755, 1650, 1625, 1555.

Mass: 418 (M+), 348, 304, 235, 207.

$[\alpha]_D^{20}$ −69.1° (C=1, methanol)

REFERENCE EXAMPLE 27 (STARTING MATERIAL FOR EXAMPLE 25)

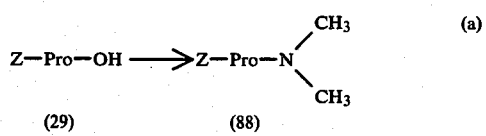

In 80 ml of dry THF were dissolved 4.9 g (20 m mol) of N-benzyloxycarbonyl-L-proline (29) and 3.5 g (26 m mole) of HOBT and then 4.53 g (22 m mol) of DCC was slowly added to the solution at 0° C. After stirring the mixture for 30 minutes at the same temperature, 10 ml of solution 2M dimethylamine tetrahydrofuran was added. The resulting mixture was allowed to stand for 12 hours at room temperature. THF was distilled off from the reaction mixture under reduced pressure, the residue thus formed was dissolved in 200 ml of ethyl acetate, and the solution was washed, in succesion, with 75 ml of an aqueous solution of 0.5N hydrochloric acid, 75 ml of a saturated aqueous sodium hydrogencarbonate solution, and 50 ml of water. After drying the organic layer with anhydrous magnesium sulfate, ethyl acetate was distilled off and the residue thus formed was purified by silica gel column chromatography (400 ml of Wako gel C-200, ethyl acetate) to provide 4.8 g of (S)-1-benzyloxycarbonyl-N,N-dimethyl-2-pyrrolidinecarboxamide (88) having a melting point of 66°–67° C.

NMR: 100 MHz (DMSO-d$^6$) $\delta_{ppm}$: 1.50–2.40 (m, 4H, proline ring), 2.74, 2.78, 2.86, 2.98 (s, s, s, s, 6H, N-dimethyl), 3.38 (m, 2H, proline ring), 4.70 (m, 1H, methine), 4.96 and 5.02 (q and s, 2H, benzyl).

IR (KBr) cm$^{-1}$: 3020, 2960, 2940, 2860, 1700, 1640.

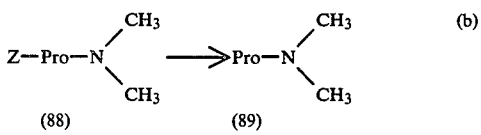

In 86 ml of ethanol was dissolved 4.3 g of compound (88) and after adding thereto 210 mg of 10% palladium-carbon, the mixture was stirred vigorously for 90 minutes in a hydrogen stream. After filtering off the catalyst, ethanol was distilled off under reduced pressure to provide 2.19 g of crude (S)-N,N-dimethyl-2-pyrrolidinecarboxamide (89).

NMR: 90 MHz (CDCl$_3$) $\delta_{ppm}$: 1.40–2.40 (m, 4H, proline ring), 2.84 (s, 1H, NH), 3.00 (s, 3H, N-methyl), 3.04 (m, 3H, N-methyl), 3.80–4.00 (m, 1H, methine).

IR (neat) cm$^{-1}$: 3280, 2940, 2850, 1635.

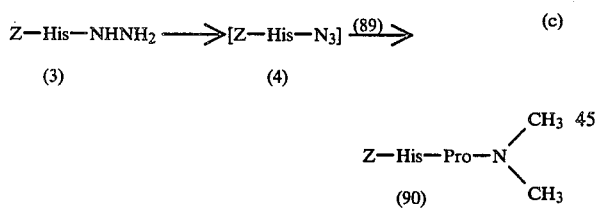

In 53.3 ml of an aqueous solution of 1N hydrochloric acid was dissolved 5.38 g (14.8×1.2 m mol) of L-z-histidine hydrazide (3) and after adding thereto 71 ml of ethyl acetate, the mixture was cooled to 0° C. Then, 5.33 ml of an aqueous solution of 4N-NaNO$_2$ was added to the mixture at the same temperature followed by stirring for 5 minutes and after adding thereto 21.3 ml of an aqueous solution of 50% potassium carbonate followed by stirring for 3 minutes, the ethyl acetate layer thus formed was collected. The aqueous layer was extracted with 18 ml of cooled ethyl acetate, the extract was combined with the foregoing ethyl acetate layer and the mixture was dried by anhydrous sodium sulfate for 5 minutes with stirring under ice-cooling.

After filtering off sodium sulfate, the filtrate was cooled to −20° C. and a solution of 2.10 g (14.8 m mol) of compound (89) dissolved in 10 ml of ethyl acetate was added slowly dropwise to the foregoing solution. The mixture was allowed to stand overnight in a refrigerator at 4° C. Ethyl acetate was distilled off under reduced pressure and the residue was purified by silica gel column chromatography (600 ml of Wako gel C-200, chloroform-methanol-conc. aqueous ammonia (10:1:0.1)) to provide 5.86 g of oily N$^\alpha$-benzyloxycarbonyl-L-histidyl-N,N-dimethyl-L-prolinamide (90).

NMR: 90 MHz (CDCl$_3$) $\delta_{ppm}$: 1.60–2.40 (m, 4H, proline ring), 3.05 (s, 3H, N-methyl), 3.16 (s, 3H, N-methyl), 4.40–5.00 (m, 2H, methine), 5.12 (s, 2H, benzyl), 5.64 (m, 1H, amide), 6.90 (s, 1H, imidazole ring), 7.38 (s, 5H, benzene ring), 7.56 (s, 1H, imidazole ring), 11.70 (m, 1H, imidazole-NH).

IR (neat) cm$^{-1}$: 3250, 2950, 2840, 1710, 1635.

Mass: 413 (M+), 341, 332, 272, 262, 244.

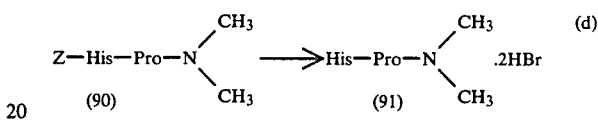

In 15 ml of acetic acid was dissolved 4.13 g (10 m mol) of compound (90) and after adding thereto 30.12 g of an acetic acid solution of 25% hydrobromic acid under ice-cooling, the mixture was stirred for 1.5 hours at room temperature. To the reaction mixture was added 450 ml of dry ether and the precipitates thus deposited were collected by filtration to provide 3.75 g of L-histidyl-N,N-dimethyl-L-prolinamide 2-hydrobromide (91).

EXAMPLE 25

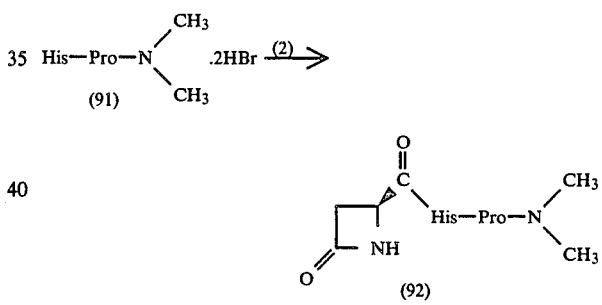

[SOLUTION A]

In 10 ml of dry DMF was dissolved 230 mg (2 m mol) of compound (2) followed by cooling to 0° C. and after adding thereto, in succesion, 351 mg of HOBT and 453 mg of DCC with stirring, the mixture was stirred for 40 minutes at the same temperature.

[SOLUTION B]

In 13 ml of dry DMF was dissolved 966 mg (2 m mol) of compound (91) followed by cooling to −15° C., and after slowly adding 404 mg of triethylamine to the solution with stirring, the mixture was stirred for 30 minutes. Thereafter, triethylamine hydrobromide was filtered off under cooling.

To solution A cooled to 0° C. was added solution B cooled to −15° C. and after stirring the mixture for 2 hours at −10° C., the mixture was allowed to stand overnight in a refrigerator at 4° C.

The reaction mixture was allowed to raise to room temperature and insoluble matters deposited were filtered off. DMF was distilled off from the filtrate under reduced pressure and the residue thus formed was purified by silica gel column chromatography (400 ml of Wako gel C-200, 400 ml, chloroform-methanol-aqueous ammonia (100:10:1)) to provide 520 mg of the colorless crystals of N$^\alpha$-[(S)-2-azetidinone-4-carbonyl]-1-histidyl-N,N-dimethyl-L-prolinamide (91) having a melting point of 133°–140° C.

NMR: 90 Mhz (D$_2$O) $\delta_{ppm}$: 1.60–2.50 (m, 4H, proline ring), 2.71 (d,d, 1H, azetidinone ring, 3-position), 2.92 (s, 1N, N-methyl), 3.17 (s, 1H, N-methyl), 4.15 (d, d, 1H, azetidinone ring, 4-position), 7.40 (s, 1H, imidazole ring), 7.74 (s, 1H, imidazole ring).

IR (KBr) cm$^{-1}$: 3180, 1755, 1630, 1560.

Mass: 376 (M+), 306, 262, 235, 207.

[$\alpha$]$_D^{20}$ −73.1° (C=1, methanol)

REFERENCE EXAMPLE 20 (STARTING MATERIAL FOR EXAMPLE 26)

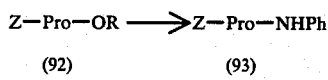
(92) (93)     (a)

In 50 ml of THF was dissolved 4.99 g of N-benzyloxycarbonyl-L-proline (20) and after adding thereto 2.23 g of triethylamine and 2.39 g of ethyl chloroformate, the reaction was maintained for 20 minutes under ice-cooling. To the reaction mixture was added 2.79 g of aniline and the reaction was performed for one hour under ice-cooling. The solvent was distilled off, the residue thus formed was dissolved in ethyl acetate, and the solution was washed, in succession, with an aqueous solution of 1N hydrochloric acid, a saturated aqueous sodium hydrogen, carbonate solution, and then a saturated aqueous sodium chloride solution. The organic layer thus formed was dried by anhydrous sodium sulfate and then concentrated to dryness. The residue was recrystallized from chloroform-ethyl acetate-hexane to provide 5.20 g of (S)-1-benzyloxycarbonyl-N-phenyl-2-pyrrolidinecarboxamide (93) having a melting point of 143°–144° C.

NMR (CDCl$_3$) $\delta_{ppm}$: 6.9–7.7 (10H), 5.17 (s, 2H), 4.43 (t, 1H), 3.4–3.8 (2H), 1.7–2.5 (4H).

IR (KBr) cm$^{-1}$: 3260, 1690, 1660, 1595, 1545.

Mass (EI): 324 (M+), 204, 160, 91, 70.

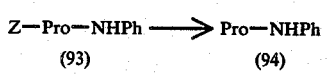
(93) (94)     (b)

In 150 ml of methanol was dissolved 4.87 g of compound (93) and the compound was hydrogenated using 487 mg of 10% palladium-carbon as a catalyst. The catalyst was filtered off and the filtrate was concentrated to provide 2.79 g of (S)-N-phenyl-2-pyrrolidinecarboxamide (94).

NMR (CDCl$_3$) $\delta_{ppm}$: 9.5–10.0 (1H), 6.95–7.75 (10H), 3.86 (dd, 1H), 2.75–3.25 (2H), 1.5–2.5 (5H) [IR (KBr) cm$^{-1}$: 3340, 3220, 2950, 2850, 1660, 1595, 1515]

Mass (EI): 190 (M+), 93, 70.

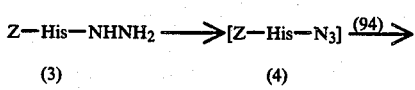
(3) (4)     (c)

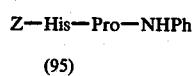
(95)

To 45 ml of an ethyl acetate solution of N$^\alpha$-benzyloxycarbonyl-L-histidine azide (4) prepared from 3.03 g of N$^\alpha$-benzyloxycarbonyl-L-histidine hydrazide (3) by a known method was added 1.52 g of compound (94) under ice-cooling and the reaction was maintained overnight in a refrigerator. The reaction mixture was concentrated and the residue thus formed was subjected to silica gel column chromatography. By eluting the product with chloroform-methanol (95:5), 2.49 g of N$^\alpha$-benzyloxycarbonyl-L-histidyl-N-phenyl-L-prolinamide (95) was obtained.

NMR (CDCl$_3$) $\delta_{ppm}$: 6.9–7.7 (11H), 6.78 (s, 1H), 5.86 (d, 1H), 5.08 (s, 2H), 4.5–4.8 (2H), 2.8–3.9 (4H), 1.5–2.5 (4H).

IR (KBr) cm$^{-1}$: 3250, 2950, 1700, 1630, 1590, 1535.

Mass (EI): 461 (M+), 342, 310, 272, 245, 191, 136, 107, 91, 70.

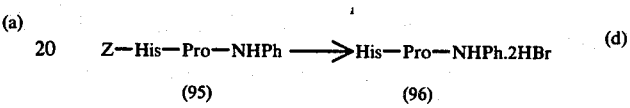
(95) (96)     (d)

To 1.79 g of compound (95) was added 19 ml of 25% hydrobromic acid—acetic acid cooled in an ice bath followed by stirring one hour at room temperature.

The reaction mixture was added to 190 ml of desiccated ether and precipitates thus formed were quickly collected by filtration and dried overnight in a desiccator containing potassium hydroxide to provide 2.05 g of L-histidyl-N-phenyl-L-prolinamide.2-hydrobromide (96).

EXAMPLE 26

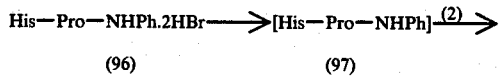
(96) (97)

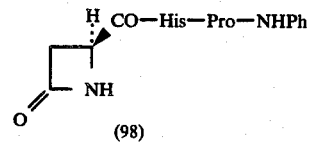
(98)

In 10 ml of DMF was dissolved 979 mg of compound (96) and after cooling the solution to −40° C., 415 mg of triethylamine was added to the solution. After maintaining the reaction for one hour at −30° C. to −40° C., the precipitates thus formed were filtered off to provide a DMF solution of L-histidyl-N-phenyl-L-prolinamide (97). The product was used for the subsequent reaction immediately after the formation thereof.

In 5 ml of DMF was dissolved 230 mg of (S)-2-azetidinone-4-carboxylic acid (2) and after adding thereto 406 mg of HOBT and 495 mg of DCC under ice-cooling, the reaction was maintained for one hour at 0° C.

The reaction mixture was cooled to −40° C. and after adding thereto a DMF solution of the foregoing compound (97), the reaction was maintained for 30 minutes at −40° C. and then overnight in a refrigerator. Precipitates were filtered off, the filtrate was concentrated to dryness, and the residue was subjected to silica gel column chromatography. By eluting the product with chloroform-methanol-aqueous ammonia (80:20:2), 652 mg of N$^\alpha$-[(S)-2-azetidinone-4-carbonyl]-L-histidyl-N-phenyl-L-prolinamide (98) was obtained.

NMR (CD₃OD) $\delta_{ppm}$: 6.9–7.7 (7H), 4.56 (dd, 1H) 4.12 (dd, 1H), 3.7–3.9 (1H), 2.81 (dd, 1H), 1.7–2.3 (4H).

IR (KBr) cm⁻: 3250, 2910, 1750, 1620, 1540.

Mass (EI): 425 (M⁺+1), 305, 262, 250, 208, 191, 154, 93, 70.

$[\alpha]_D^{25} = -103.5°$ (C=1.35, methanol)

REFERENCE EXAMPLE 29 (RAW MATERIAL FOR EXAMPLE 27)

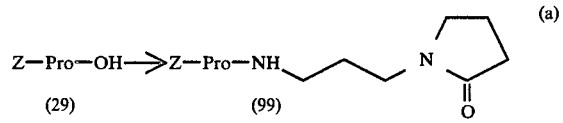
(a)

In 100 ml of THF was dissolved 9.97 g of compound (29) and after adding slowly thereto 4.45 g of triethylamine and then 6.01 g of isobutyl chloroformate under ice-cooling, the reaction was performed under ice-cooling. To the reaction mixture was slowly added 11.37 g of 3-(2-oxo-1-pyrrolidinyl)-propylamine and then the reaction was performed for one hour under ice-cooling. Precipitates were filtered off, the filtrate was concentrated, and the residue thus formed was subjected to silica gel column chromatography. By eluting the product with ethyl acetatemethanol (4:1), 4.43 g of (S)-1-benzyloxycarbonyl-N-[3-(2-oxo-pyrrolidinyl)propyl]-2-pyrrolidine carboxamide (99) was obtained.

NMR (CDCl₃) $\delta_{ppm}$: 7.36 (s, 5H), 5.16 (2H), 4.33 (t, 1H), 2.8–3.8 (8H), 1.7–2.5 (10H).

IR (neat) cm⁻¹: 3280, 2930, 2860, 1700, 1660, 1530.

Mass (EI): 373 (M⁺), 238, 204, 160, 91, 70

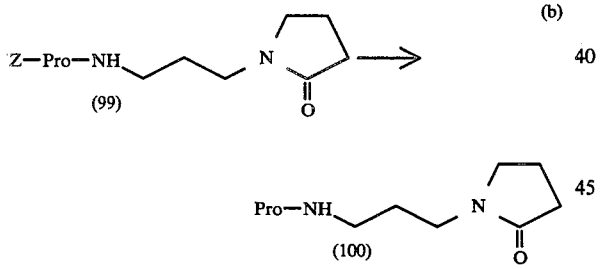
(b)

(c)

In 150 ml of methanol was dissolved 4.32 g of compound (99) and the compound was hydrogenated using 432 mg of 10% palladium-carbon as a catalyst. Then, the catalyst was filtered off from the reaction mixture and the filtrate was concentrated to provide 1.99 g of (S)-N-[3-(2-oxo-1-pyrrolidinyl)propyl]-2-pyrrolidinecarboxamide (100).

NMR (CDCl₃) $\delta_{ppm}$: 7.6–8.2 (1H), 3.72 (d, d, 1H), 2.8–3.5 (8H), 1.5–2.5 (10H).

IR (neat) cm⁻¹: 3280, 2920, 2850, 1650, 1530.

Mass (EI): 239 (M⁺), 197, 141, 99, 70.

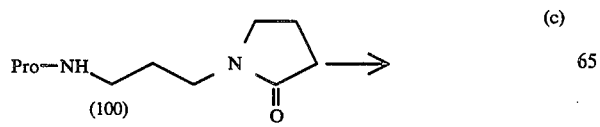

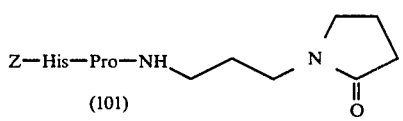
(101)

To 30 ml of a ethyl acetate solution of compound (4) prepared from 2.12 g of compound (3) by a known method was added 5 ml of a DMF solution of 1.17 g of compound (100) under ice-cooling and the reaction was maintained overnight in a refrigerator. The reaction mixture was concentrated and the residue thus formed was subjected to silica gel column chromatography. By eluting the product with chloroform-methanol-aqueous ammonia (90:10:1), 2.00 g of N^α-benzyloxycarbonyl-L-histidyl-N-[3-(2-oxo-1-pyrrolidinyl)-propyl]-L-prolinamide (101) was obtained.

NMR (CDCl₃) $\delta_{ppm}$: 8.0–8.4 (1H), 7.56 (1H), 7.35 (s, 5H), 6.97 (s, 1H), 5.87 (d, 2H), 5.10 (s, 2H), 4.3–4.8 (2H), 2.9–3.7 (8H), 1.5–2.6 (10H).

IR (KBr) cm⁻¹: 3220, 2930, 2850, 1700, 1640, 1530.

Mass (EI): 510 (M⁺), 430, 402, 359, 267, 239, 136, 108, 79.

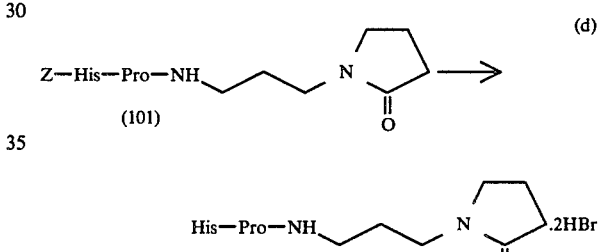
(d)

To 1.02 g of compound (101) was added 10 ml of an ice-cooled acetic acid solution of 25% hydrobromic acid and the reaction was performed for 2 hours at room temperature. The reaction mixture was added to 100 ml of dry ether and then the precipitates thus formed were quickly collected by filtration and dried overnight in a desicator containing potassium hydroxide, 1.28 g of L-histidyl-N-[3-(2-oxo-1-pyrrolidinyl)-propyl]-L-prolinamide.2-hydrobromide (102) was obtained.

EXAMPLE 27

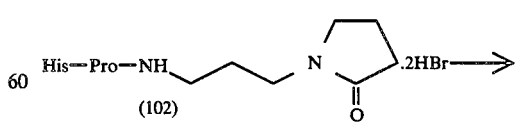

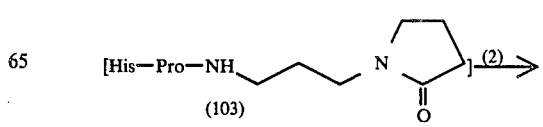

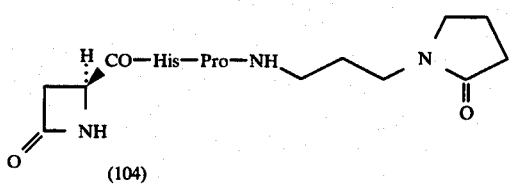

In 10 ml of DMF was dissolved 1.28 g of compound (102) and after cooling to −40° C., 415 mg of triethylamine was added to the solution. After maintaining the reaction for one hour at −30° to −40° C., the precipitates thus formed were filtered off to provide a DMF solution of L-histidyl-N-[3-(2-oxo-1-pyrrolidinyl)-propyl]-L-prolinamide (103). The product was used for the subsequent reaction immediately after the formation thereof.

In 5 ml of DMF was dissolved 230 mg of compound (2) and after adding thereto 406 mg of HOBT and 495 mg of DCC, the reaction was maintained for one hour under ice-cooling. The reaction mixture was cooled to −40° C. and after adding thereto the foregoing DMF solution of compound (103), the reaction was maintained for 30 minutes at −40° C. and then overnight in a refrigerator. Precipitates thus formed were filtered off, the filtrate was concentrated to dryness, and the residue was subjected to silica gel column chromatography. By eluting the product with chloroform-methanol-aqueous amonnia (80:20:2), 461 mg of $N^\alpha$-[(S)-2-azetidinone-4-carbonyl]-L-histidyl-N-[3-(2-oxo-1-pyr-rolidinyl)propyl]-L-prolinamide (104) was obtained.

NMR ($D_2O$) $\delta_{ppm}$: 7.74 (1H), 7.05 (1H), 5.96 (dd, 1H), 5.2–5.5 (2H), 2.9–3.9 (11H), 2.72 (dd, 1H), 1.6–2.6 (10H).
IR (KBr) cm$^{-1}$: 3240, 2950, 2850, 1755, 1630.
Mass (EI): 473 (M+), 304, 262, 235, 154, 70.
$[\alpha]_D^{27}$: −75.6° (C=0.55, methanol).

REFERENCE EXAMPLE 30

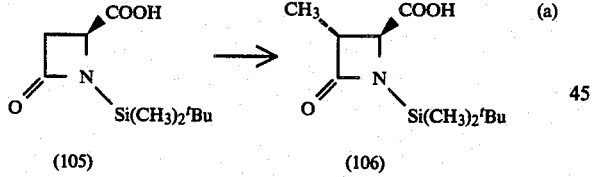

In 6 ml of dry THF was dissolved 836.3 mg (8.28 m mol) of diisopropylamine and the solution was cooled to 0° C. under a nitrogen atmosphere. To the solution was added 5.2 ml of a n-hexane solution containing 530 mg (8.28 m mol) of n-butyl lithium at 0° C. and the mixture was stirred for 10 minutes at the same temperature. To the solution was added a solution of 920 mg (4 m mol) of (S)-1-t-butyldimethylsilyl-2-azetidinone-4-carboxylic acid (105) dissolved in 8 ml of dry THF at 0° C. and then the mixture was stirred for 30 minutes at room temperature. The solution was cooled to 0° C. and after adding thereto 682 mg (4.8 m mol) of methyl iodide, the mixture was stirred for 30 minutes at room temperature. The reaction mixture thus obtained was cooled again to 0° C., acidified with the addition of an aqueous 10% citric acid solution, and after addition of ether and water, the organic layer was separated. The ether layer was separated from the aqueous layer, dried, and the solvent was distilled off to provide 860 mg of 1-t-butyl-dimethylsilyl-3(R)-methyl-2-azetidinone-4(S)-carboxylic acid (106) as colorless crystals.

$[\alpha]_D^{23}$= −36.1° (C=0.5, methanol).

NMR (90 MHz, CDCl$_3$) $\delta_{ppm}$: 0.16 (3H, s, Si-methyl), 0.34 (3H, s, Si-methyl), 0.98 (9H, s, t-butyl), 1.42 (3H, d, azetidinone ring 3-position methyl), 3.37 (1H, q, d, azetidinone ring 3-position), 3.74 (1H, d, J=3.5 Hz, azetidinone ring 4-position), 9.60 (1H, s, carboxy group).

IR (KBr) cm$^{-1}$: 2940, 2920, 2840, 1740, 1680.
Mass m/z: 244 (M+1), 200, 186, 143.

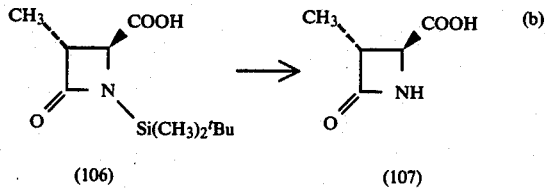

In 20 ml of a mixture of water, methanol, and concentrated hydrochloric acid (10:90:1.7) was dissolved 641 mg (2.63 m mol) of compound (106) and the solution was stirred for 1.5 hours at room temperature. The reaction mixture was cooled to 0° C., neutralized with 4 ml of an aqueous solution of 1N sodium hydroxide, and the solvent was distilled off under reduced pressure to provide 3(R)-methyl-2-azetidinone-4(S)-carboxylic acid (107), which was used in the subsequent reaction without being purified.

NMR (60 MHz, D$_2$O) $\delta_{ppm}$: 1.25 (3H, d, methyl group), 3.20 (1H, q, d, azetidinone ring 3-position), 3.88 (1H, d, azetidinone ring 4-position).

EXAMPLE 28

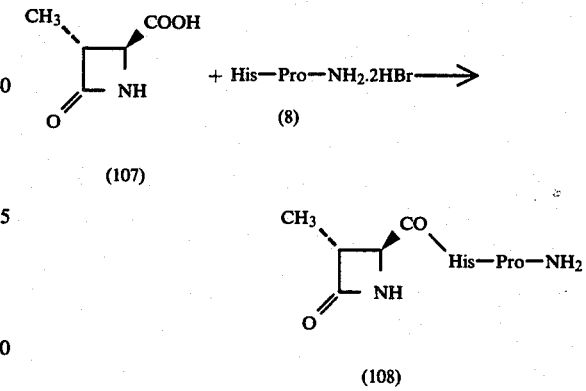

In 13 ml of dry DMF was dissolved compound (107) obtained in the foregoing step followed by cooling to 0° C. and after adding thereto 461.6 mg (3.42 m mol) of HOBT and 596 mg (2.89 m mol) of DCC, the mixture was stirred for 15 minutes at the same temperature (solution A).

In 30 ml of dry DMF was dissolved 1.086 g (2.63 m mol) of L-histidyl-L-prolinamide-2-hydrobromide (8) and after cooling the solution to −10° C., 0.733 ml (2.63 m mol) of triethylamine was added to the solution. After stirring the mixture for 30 minutes at the same temperature, triethylamine hydrobromide thus precipitated was filtered off in a nitrogen atmosphere to provide a clear filtrate (solution B).

To solution A was added solution B and the mixture was stirred overnight at 0° to 5° C. and then for 3 hours at room temperature. Crystals thus precipitated were filtered off, the filtrate was concentrated under reduced pressure, and the residue thus formed was subjected to silica gel column chromatography using 200 ml of silica gel (Wako gel C-200). By eluting the product with chloroform-methanol-aqueous ammonia (80:20:2), 200 mg of N$^\alpha$[3(R)-methyl-2-azetidinone-4(S)-carbonyl]-L-histidyl-L-prolinamide (108) was obtained.

$[\alpha]_D^{23} = -33.8°$ (C=0.5, methanol)

NMR (100 MHz, D$_2$O) $\delta_{ppm}$: 1.60–2.40 (4H, m, proline ring) 2.80–3.20 (3H, m, histidine ring, $\beta$-methylene, proline ring), 3.40–4.00 (2H, m, azetidinone ring 3-position, proline ring), 3.90 (1H, d, J=3.0 Hz, azetidinone ring 4-position), 4.40 (1H, m, methine), 4.88 (1H, m, metine), 7.00 (1H, s, imidazole ring), 7.68 (1H, s, imidazole ring), 1.32 (3H, d, methyl).

IR (KBr) cm$^{-1}$: 3450, 2960, 2860, 1750, 1670, 1630.
Mass m/z: 362 (M+), 318, 278, 249, 234, 221.

PREPARATION EXAMPLES

Injection

A lyophilized formulation containing 0.025 mg or 0.05 mg of N$^\alpha$-[(S)-2-azetidione-4-carbonyl]-L-histidyl-L-prolinamide together with 10 ml of mannitol in one ampule was prepared and each of the formulations was dissolved in 1 ml of a sterilized physiological saline solution to provide an injection.

Tablets

A mixture of 0.25 part by weight of N$^\alpha$-[(S)-2-azetidinone-4-carbonyl]-L-histidyl-L-prolinamide and 7.5 parts by weight of lactose was pulverized, and mixed uniformly with 44.4 parts by weight of lactose, 22.5 parts by weight of crystalline cellulose, and 0.4 part by weight of magnesium stearate. The resultant mixture was compacted to form tablets of 75 mg/tablet.

Capsules

A mixture of 0.5 part by weight of N$^\alpha$-[(S)-1-azetidinone-4-carbonyl]-L-histidyl-L-prolinamide and 10 parts by weight of lactose was pulverized, and mixed uniformly with 137.5 parts by weight of lactose, 60 parts by weight of corn starch, and 2.0 parts by weight of magnesium stearate. The mixture was filled into gelatin hard capsules, to provide a capsulated preparation of 210 mg/capsule.

What is claimed is:

1. A 4-substituted-2-azetidinone compound represented by general formula (VII)

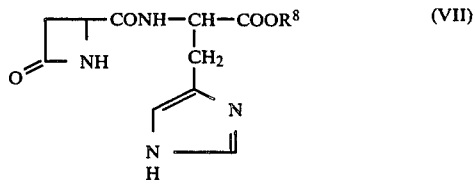

wherein R$^8$ represents a hydrogen atom, a lower alkyl, a phenyl lower alkyl or a naphthylmethyl group or a salt thereof.

* * * * *